(12) United States Patent
Jang et al.

(10) Patent No.: US 9,150,536 B2
(45) Date of Patent: Oct. 6, 2015

(54) CYCLOALKENE DERIVATIVES AND ORGANIC ELECTRONIC DEVICES USING THE SAME

(75) Inventors: Hye-Young Jang, Daejeon (KR); Jae-Chol Lee, Daejeon (KR); Jae-Soon Bae, Daejeon (KR); Jeung-Gon Kim, Daejeon (KR); Seong-So Kim, Gyeonggi-do (KR); Chang-Hwan Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1112 days.

(21) Appl. No.: 13/145,309

(22) PCT Filed: Jan. 20, 2010

(86) PCT No.: PCT/KR2010/000369
§ 371 (c)(1),
(2), (4) Date: Oct. 21, 2011

(87) PCT Pub. No.: WO2010/085087
PCT Pub. Date: Jul. 29, 2010

(65) Prior Publication Data
US 2012/0037892 A1 Feb. 16, 2012

(30) Foreign Application Priority Data
Dec. 20, 2009 (KR) .................. 10-2009-0004600

(51) Int. Cl.
*H01L 51/54* (2006.01)
*C07D 333/08* (2006.01)
*C07D 215/04* (2006.01)
*C07C 13/54* (2006.01)
(Continued)

(52) U.S. Cl.
CPC ............ *C07D 333/08* (2013.01); *C07D 209/08* (2013.01); *C07D 213/06* (2013.01); *C07D 215/06* (2013.01); *C07D 235/18* (2013.01); *H01L 51/0058* (2013.01); *H01L 51/5048* (2013.01); *Y02E 10/549* (2013.01)

(58) Field of Classification Search
None
See application file for complete search history.

(56) References Cited

U.S. PATENT DOCUMENTS

2006/0046097 A1  3/2006  Kim et al.
2007/0072002 A1  3/2007  Kim et al.
(Continued)

FOREIGN PATENT DOCUMENTS

JP  2007-084828 A   4/2007
JP  2009-249378 A  10/2009
(Continued)

OTHER PUBLICATIONS

T. Ross Kelly and Imanol Tellitu and Jose Perez Sestelo; In Search of Molecular Ratchets; Angew. Chem., International Edition in English, 1997, vol. 36, No. 17, p. 1866-1868.
(Continued)

*Primary Examiner* — Jay Yang
(74) *Attorney, Agent, or Firm* — Dentons US LLP

(57) ABSTRACT

The present invention relates to a novel cycloalkene derivative, and an organic electronic device using the same. The cycloalkene derivative according to the exemplary embodiment of the present invention may act as a hole injection, a hole transport, an electron injection, an electron transport, or a light emitting material in an organic light emitting diode and an organic electronic device, and in particular, may be used alone as a light emitting host or a dopant.

16 Claims, 6 Drawing Sheets

(51) Int. Cl.

| | |
|---|---|
| C07D 211/68 | (2006.01) |
| C07D 209/08 | (2006.01) |
| C07D 213/06 | (2006.01) |
| C07D 215/06 | (2006.01) |
| C07D 235/18 | (2006.01) |
| H01L 51/00 | (2006.01) |
| H01L 51/50 | (2006.01) |

(56) References Cited

U.S. PATENT DOCUMENTS

| | | | |
|---|---|---|---|
| 2007/0090353 | A1 | 4/2007 | Lee et al. |
| 2007/0205412 | A1 | 9/2007 | Bae et al. |
| 2008/0111473 | A1 | 5/2008 | Kawamura et al. |
| 2008/0226945 | A1 | 9/2008 | Kim et al. |
| 2008/0284325 | A1 | 11/2008 | Noh et al. |
| 2010/0001262 | A1 | 1/2010 | Kim et al. |
| 2010/0045170 | A1 | 2/2010 | Lee et al. |
| 2010/0051106 | A1 | 3/2010 | Kim et al. |
| 2010/0187512 | A1 | 7/2010 | Ito |

FOREIGN PATENT DOCUMENTS

| | | |
|---|---|---|
| JP | 2010-059144 A | 3/2010 |
| KR | 10-2006-0050915 | 5/2006 |
| KR | 10-2007-0049080 A | 5/2007 |
| KR | 10-2007-0088972 A | 8/2007 |
| KR | 10-2007-0091540 A | 9/2007 |
| KR | 10-0767571 | 10/2007 |
| KR | 10-2008-0010186 A | 1/2008 |
| KR | 10-0852118 B1 | 8/2008 |
| WO | 98-22477 A1 | 5/1998 |
| WO | WO 2006/025700 A1 | 3/2006 |
| WO | 2007-046651 A9 | 4/2007 |
| WO | WO 2007/046651 A1 | 4/2007 |
| WO | WO 2007/052985 A1 | 5/2007 |
| WO | WO 2008/013399 A1 | 1/2008 |
| WO | 2008-156052 A1 | 12/2008 |

OTHER PUBLICATIONS

Freek Van De Griendt and Hans Carfontain; Aromatic Sulphonation. Part 73. Behavior of Three 9-Alkylanthra-cenes containing One Sidechain Hydrogen in Dioxan-SO3 Complex in Dioxan as Sulphonating Medium; Journal of the Chemical Society, Perkin Transactions II, 1980, 1, p. 19-22; Laboratory for Organic Chemistry, University of Amsterdam, Nieuwe Achtergracht, 129, 1018 WS Amsterdam, The Netherlands.

Nikitin, Kirill, Joining the rings: the preparation of 2- and 3-indenyltriptycenes, and curious related processes; Organic & Biomolecular Chemistry, 2007, vol. 5, No. 12, p. 1952-1960.

Harrington, Laura E., Toward an Organometallic Molecular Brake with a Metal Foot Pedal: Synthesis, Dynamic Behavior, and X-ray Crystal Structure of [(9-Indenyl)triptycene] chromium Tricarbonyl; Organometallics, 2004, vol. 23, p. 2884-2891; Departments of Chemistry, McMaster University, 1280 Main Street West, Hamilton Ontario, Canada L85 4M1 and University College Dublin, Belfield, Dublin 4, Ireland.

Synthesis International Journal of Methods in Synthetic Organic Chemistry, Feb. 1984, No. 2, p. 161-164; Georg Thieme Verlag Stuggart; New York Thieme-Stratton Inc., New York.

Marco S. Passafaro and Brian A. Keay; A One Pot in Situ Combined Shapiro-Suzuki Reaction; Tetrahedron Letters, 1996, vol. 37, No. 4, p. 429-432; Department of Chemistry, University of Calgary, Calgary, Alberta, Canada, T2N IN4.

Fang Xie and Krishnamoorthy Sivakumar and Qingbing Zeng and Michael A. Bruckman and Black Hodges and Qian Wang; A fluorogenic 'click' reaction of azidoanthracene derivatives; Science Direct; Tetrahedron, 2008, 64, p. 2906-2914; Department of Chemistry and Biochemistry and Nanocenter, University of South Carolina, 631 Sumter Street, Columbia, SC, 29208.

T. Ross Kelly and Jose Perez Sestelo and Imanol Tellitu; New Molecular Devices: In Search of a Molecular Ratchet; The Journal of Organic Chemistry, 1998, 63, p. 3655-3665; Department of Chemistry, E.F. Merkert Chemistry Center, Boston College, Chestnut Hill, Massachusetts 02167.

J. Ern and A.T. Bend and H.-D. Martin and S. Mukamel and S. Tretlak and K. Tsyganenko and K. Kuldova and H.P. Trommsdorff and C. Kryschi; Reaction Dynamics of a Photochromic Fluorescing Dithienylethene; The Journal of Physical Chemistry A, 2001, 105, p. 1741-1749. Department of Chemistry, University of Rochester, Rochester, New York 14627.

Hidehiro Yamaguchi and Kenji Matsuda and Masahiro Irie; Excited-State Behavior of a Fluorescent and Photochromic Diarylethene on Silver Nanoparticles; The Journal of Physical Chemistry C, 2007, 111, p. 3853-3862; Department of Chemistry and Biochemistry, Graduate School of Engineering, Kyushu University, and PRESTO, JST, 744 Motooka, Nichi-ku Fukuoka 812-8581 Japan.

Office Action of European Patent Office in Application No. 10733640.6 dated Mar. 13, 2013.

Office Action of Chinese Patent Office in Application No. 201080005081.4 dated May 6, 2013.

CYCLOALKENE DERIVATIVES AND ORGANIC ELECTRONIC DEVICES USING THE SAME

This application is a national stage application of PCT/KR2010/000369, filed Jan. 20, 2010, which claims the priority to Korean Patent Application No. KR 10-2009-0004600, filed Jan. 20, 2009, which is hereby incorporated by reference in its entirety.

DISCLOSURE

1. Technical Field

The present invention relates to novel cycloalkene derivatives, and organic electronic devices using the same.

2. Background Art

An organic electronic device means a device that requires exchanging of electric charges between electrodes using holes and/or electrons and organic materials. The organic electronic device may be largely divided into the following two categories according to an operation principle. First, there is an electronic device in which an exiton is formed in an organic material layer by a photon that flows from an external light source to the device, the exiton is separated into electrons and holes, and the electrons and the holes are transferred to the different electrodes, respectively, and used as a current source (voltage source). Second, there is an electronic device in which holes and/or electrons are injected into an organic material semiconductor forming an interface in respect to the electrode by applying voltage or current to two or more electrodes, and the device is operated by the injected electrons and holes.

As examples of the organic electronic device, there are an organic light emitting diode, an organic solar cell, an organic photoconductor (OPC), an organic transistor and the like, and these device s require a hole injection or transport material, an electron injection or transport material or a light emitting material in order to drive the device.

Hereinafter, an organic light emitting diode will be mainly described in detail. However, in the organic electronic devices, the hole injection or transport material, the electron injection or transport material or the light emitting material are operated on the basis of the similar principle.

In general, an organic light emitting phenomenon means a phenomenon that converts electric energy into light energy by using an organic material. The organic light emitting diode using the organic light emitting phenomenon has a structure which generally includes an anode, a cathode, and an organic layer disposed therebetween. Herein, most organic material layers have a multilayered structure that includes different materials in order to increase efficiency and stability of the organic light emitting diode, and may include, for example, a hole injection layer, a hole transport layer, a light emitting layer, an electron transport layer, an electron injection layer and the like. In the organic light emitting diode structure, if voltage is applied between two electrodes, holes are injected from an anode to the organic material layer and electrons are injected from a cathode to the organic material layer, and when the injected holes and the electrons meet each other, an exciton is formed, and light is emitted when the exciton falls to a bottom state. It is known that this organic light emitting diode has properties such as magnetic light emission, high brightness, high efficiency, low driving voltage, a wide viewing angle, high contrast, high speed response and the like.

In the organic light emitting diode, the material that is used as the organic material layer may be classified into a light emitting material and an electric charge transport material, for example, a hole injection material, a hole transport material, an electron transport material, an electron injection material, and the like, according to a function thereof. The light emitting material may be classified into a high molecule type and a low molecule type according to the molecular weight, and a fluorescent material derived from a singlet excitation state of an electric field and a phosphorescent material derived from a triplet excitation state of an electric field according to a mechanism of light emission. In addition, the light emitting material may be classified into blue, green, and red light emitting materials according to the emission color and yellow and orange light emitting materials in order to implement better natural colors.

Meanwhile, in the case where only one material is used as the light emitting material, a maximum light emitting wavelength may be moved to a long wavelength by interaction between molecules, and a color purity may be decreased or efficiency of the diode may be decreased by a light emitting reduction effect. Accordingly, in order to increase color purity and increase emission efficiency through transferring of energy, a host/dopant system may be used as the light emitting material. The principle is that if a small amount of dopant that has a smaller energy band gap than a host forming the light emitting layer is mixed with the light emitting layer, the exciton that is generated from the light emitting layer is transported to the dopant to emit light at high efficiency. In this case, since the wavelength of the host is moved to the wavelength bandwidth of the dopant, a desired wavelength of light may be obtained according to the kind of used dopant.

In order to allow the organic light emitting diode to sufficiently show the above excellent properties, a material constituting the organic material layer in the diode, for example, the hole injection material, the hole transport material, the light emitting material, the electron transport material, the electron injection material and the like should be supported by stable and efficient materials. However, the development of a stable and efficient organic material layer material for organic light emitting diodes has not yet been made. Therefore, there is a demand for developing a novel material, and the necessity for developing the novel material is similarly applied even to another organic electronic device described above.

DISCLOSURE

Technical Problem

The present invention has been made in an effort to provide a novel stable and efficient cycloalkene derivative and an organic electronic device using the same.

Technical Solution

An exemplary embodiment of the present invention provides a compound represented by the following Formula 1.

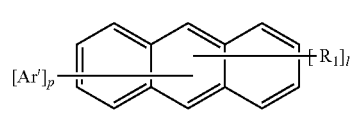

[Formula 1]

wherein
$R_1$ is a substituent group represented by $—[Ar]_m—X$,
p is an integer of 0 to 3, l is an integer of 1 to 4, and m is an integer of 0 to 5, Ar is a substituted or unsubstituted $C_6$-$C_{50}$ arylene group or a substituted or unsubstituted $C_2$-$C_{50}$ divalent heterocyclic group including N, O or S as a heteroelement, Ar' is a substituted or unsubstituted $C_6$-$C_{50}$ aryl group or a substituted or unsubstituted $C_2$-$C_{50}$ heterocyclic group including N, O or S as a heteroelement, X is a substituent group selected from the following Structural Formulas,

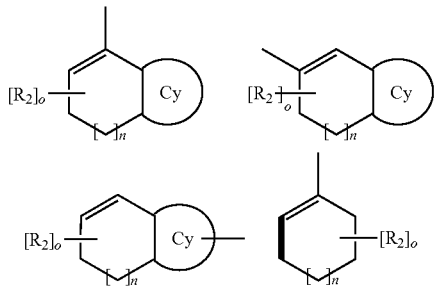

in the Structural Formulas, Cy is a substituted or unsubstituted $C_6$-$C_{50}$ aryl group or a substituted or unsubstituted $C_2$-$C_{50}$ heterocyclic group including N, O or S as a heteroelement, $R_2$ is selected from the group consisting of a substituted or unsubstituted $C_1$-$C_{40}$ alkyl group; a substituted or unsubstituted $C_1$-$C_{40}$ alkoxy group; a substituted or unsubstituted $C_2$-$C_{40}$ alkenyl group; a substituted or unsubstituted $C_6$-$C_{50}$ aryl group; a substituted or unsubstituted $C_6$-$C_{50}$ arylamine group; a substituted or unsubstituted $C_2$-$C_{50}$ heteroarylamine group including N, O or S as a heteroelement; a substituted or unsubstituted $C_2$-$C_{50}$ heterocyclic group including O, N or S as a heteroelement; a substituted amino group; a nitrile group; a nitro group; a halogen group; and an amine group, n is an integer of 0 to 5, O is an integer of 0 to 10, and in the case where O is 2 or more, $R_2$s may be the same as or different from each other, and in the case where l, m or p is 2 or more, Ar, Ar', or $R_1$ may be the same as or different from each other.

Another exemplary embodiment of the present invention provides an organic electronic device which includes a first electrode, a second electrode, and one or more organic material layers that are disposed between the first electrode and the second electrode, wherein one or more layers of the organic material layers include the compound represented by Formula 1.

Advantageous Effects

The compound according to exemplary embodiments of the present invention may act as a hole injection, hole transport, electron injection and transport, or light emitting material in an organic light emitting diode and an organic electronic device, and the organic electronic device according to the exemplary embodiment of the present invention shows excellent properties in terms of efficiency, a driving voltage, and stability.

BEST MODE

Figure 1:
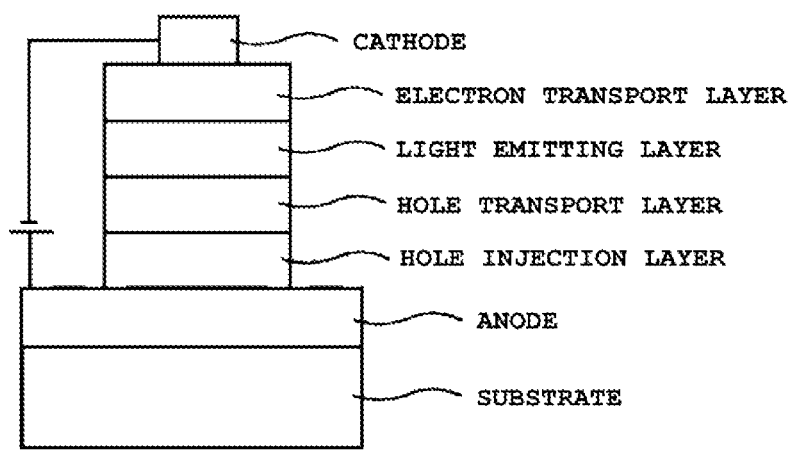
FIG. 1 is a schematic view that illustrates a structure of an organic light emitting diode according to an exemplary embodiment of the present invention.
Figure 2:
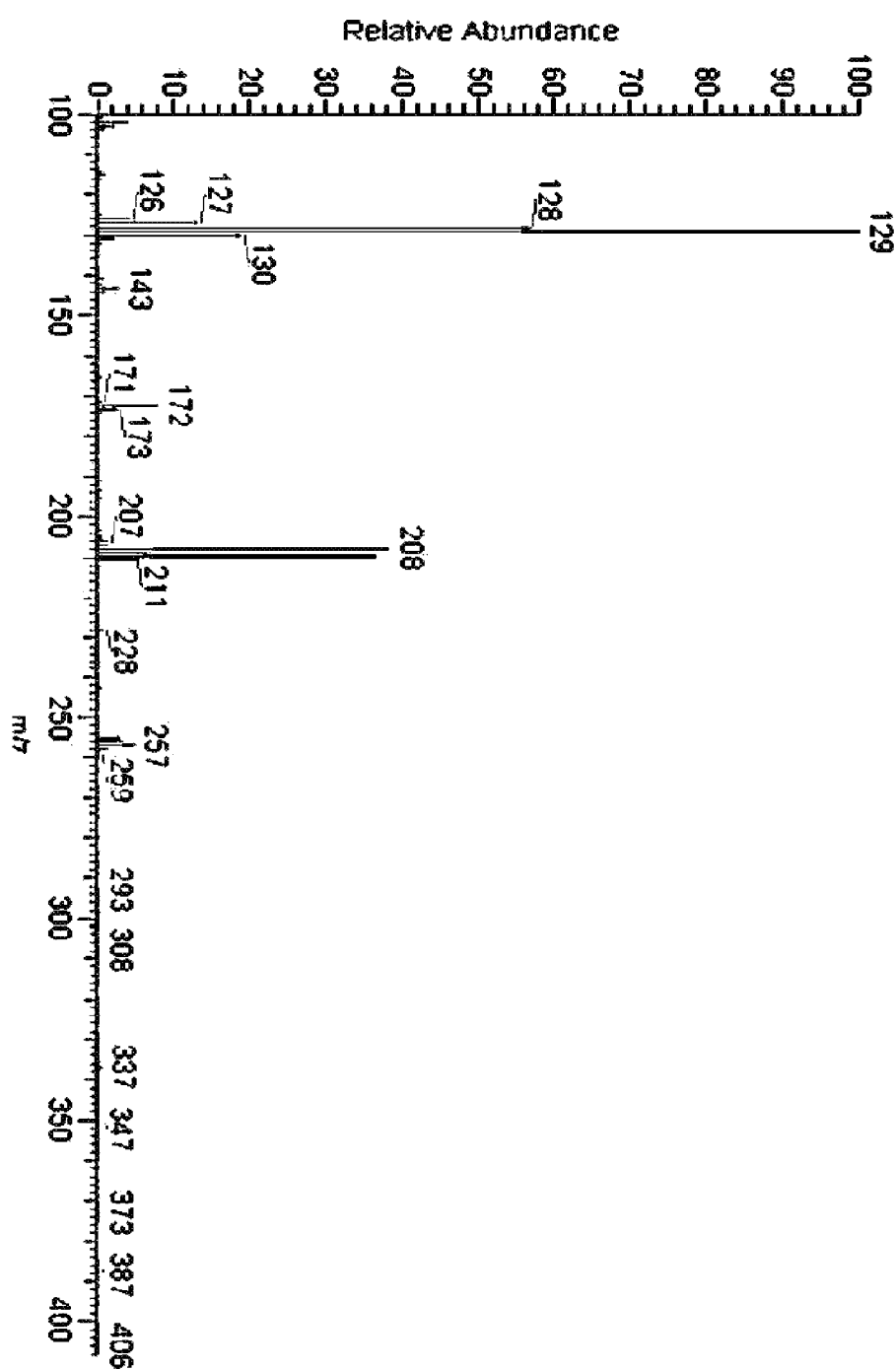
FIG. 2 is a MS spectrum of compound A that is manufactured in Preparation Example 1 of the present invention.
Figure 3:
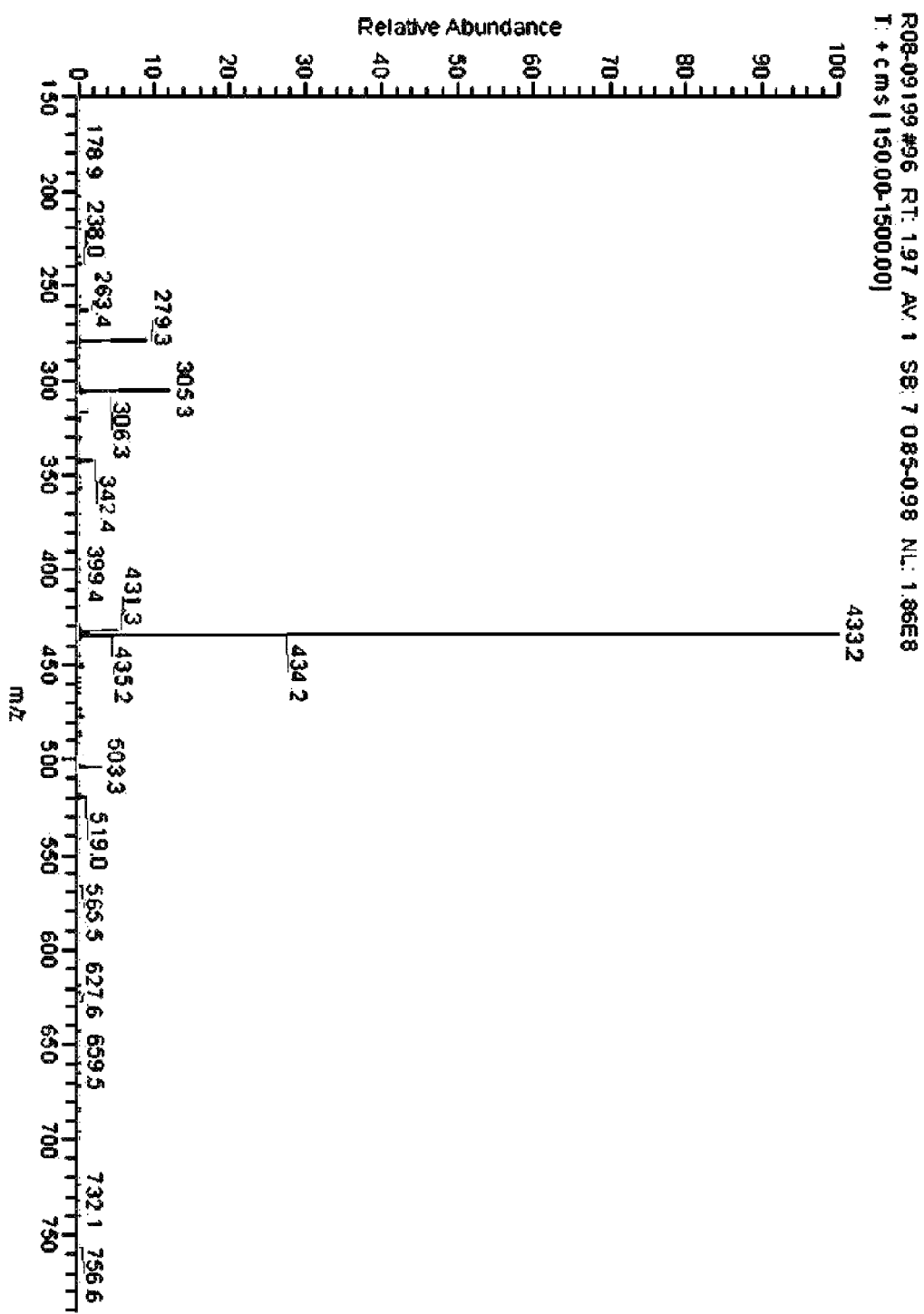
FIG. 3 is a MS spectrum of compound 2 that is manufactured in Preparation Example 2 of the present invention.
Figure 4:
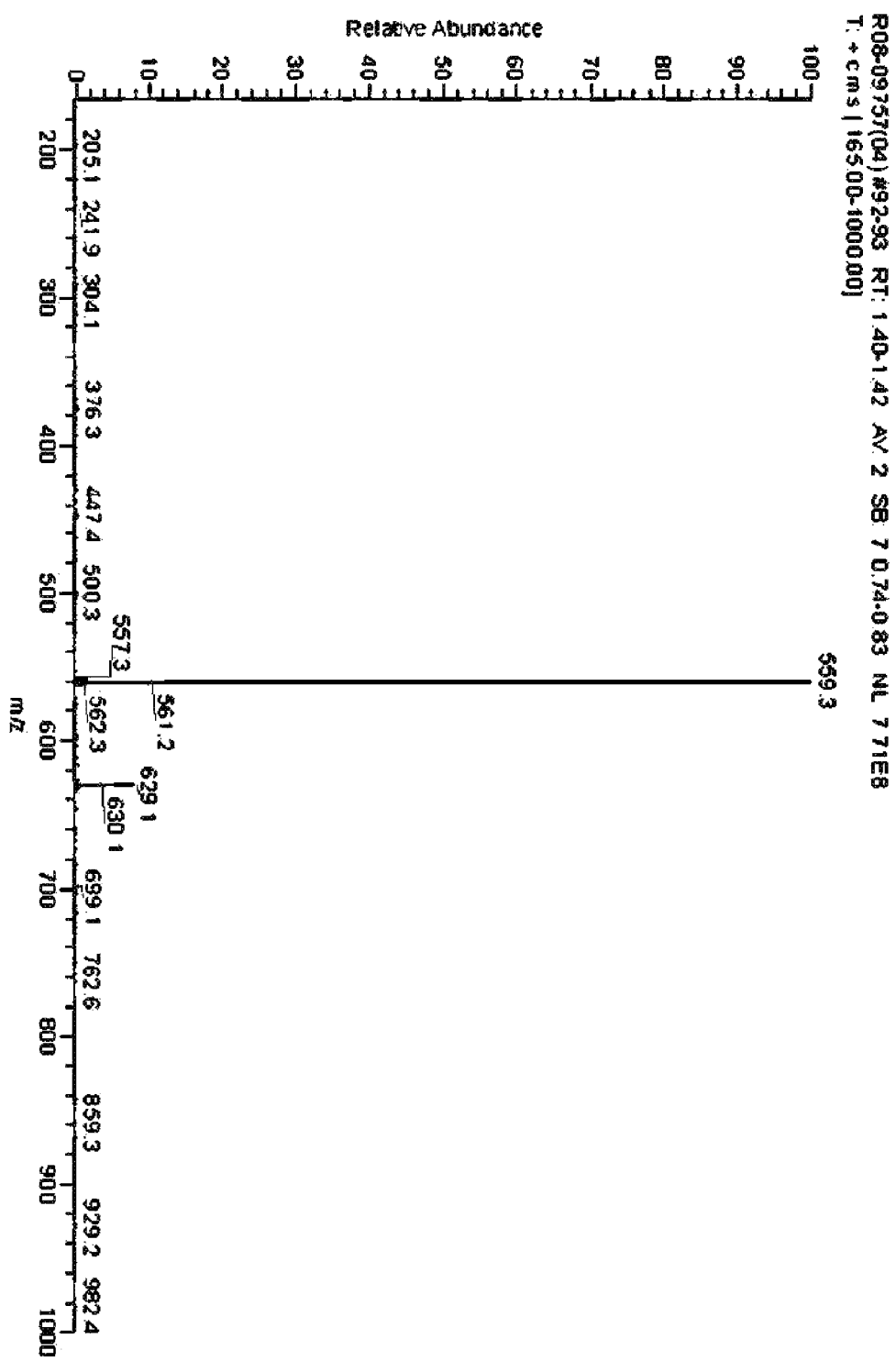
FIG. 4 is a MS spectrum of compound 77 that is manufactured in Preparation Example 3 of the present invention.
Figure 5:
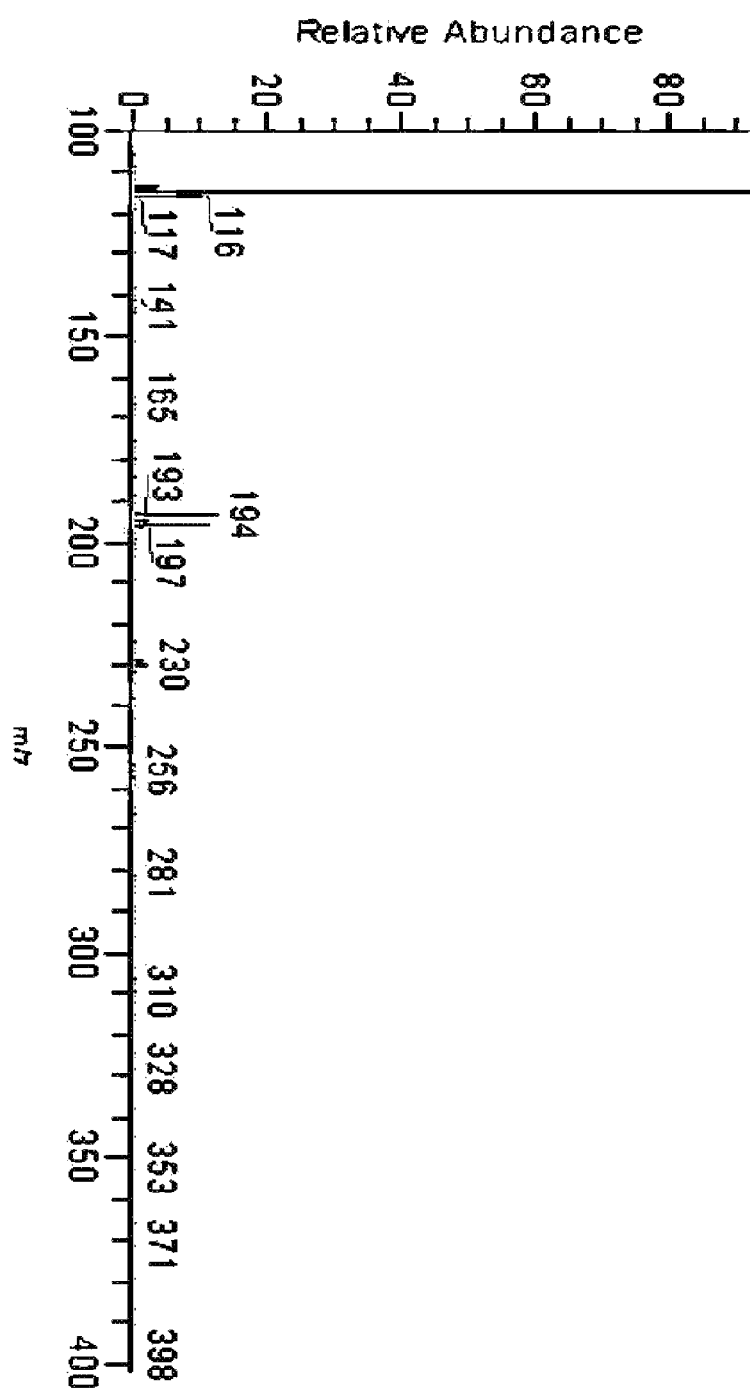
FIG. 5 is a MS spectrum of compound C that is manufactured in Preparation Example 4 of the present invention.
Figure 6:
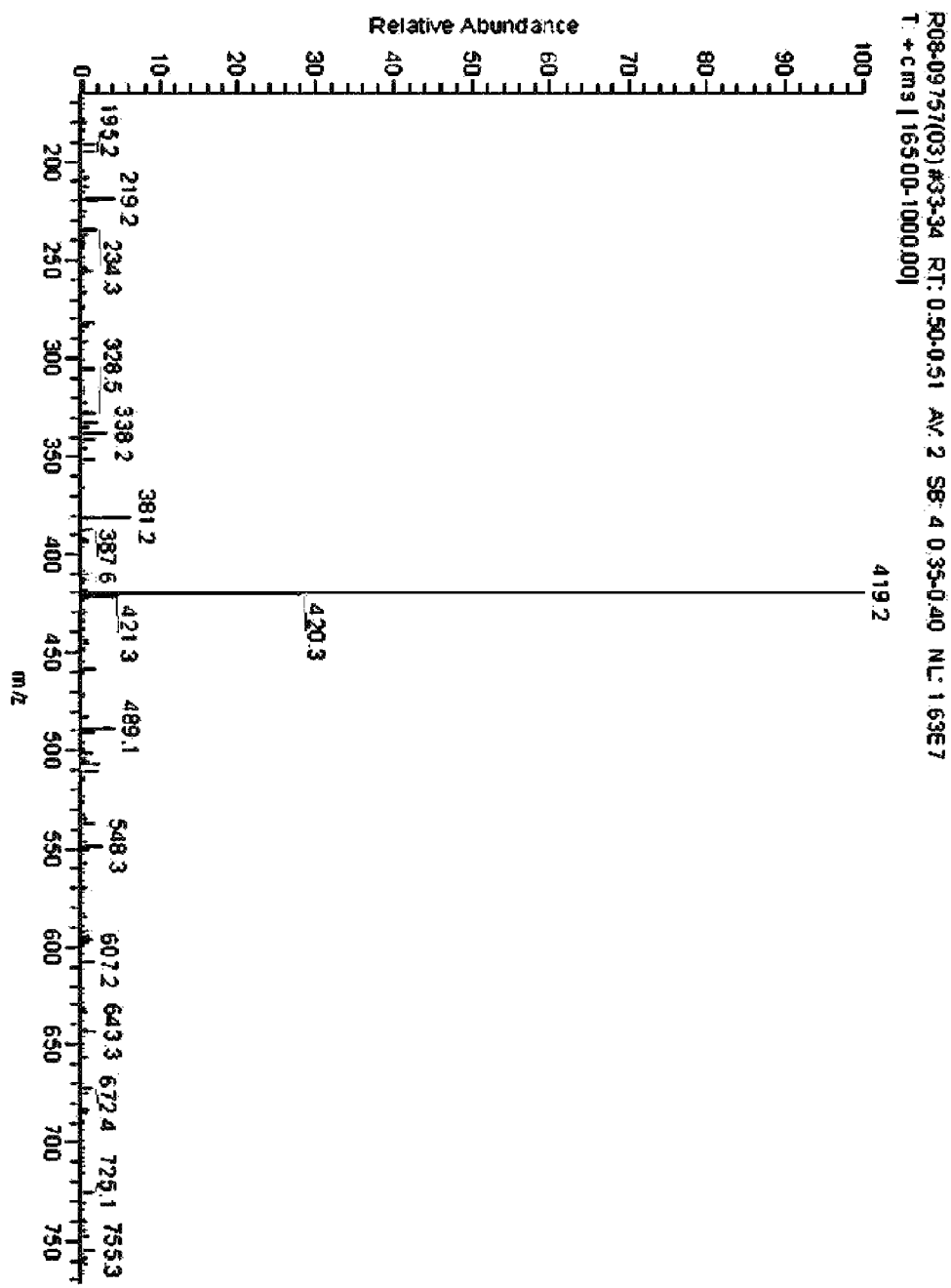
FIG. 6 is a MS spectrum of compound 10 that is manufactured in Preparation Example 5 of the present invention.

Hereinafter, the present invention will be described in more detail.

An exemplary embodiment of the present invention relates to a compound represented by Formula 1.

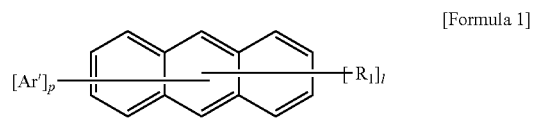

[Formula 1]

wherein $R_1$ is a substituent group represented by —[Ar]$_m$—X, p is an integer of 0 to 3, l is an integer of 1 to 4, and m is an integer of 0 to 5, Ar is a substituted or unsubstituted $C_6$-$C_{50}$ arylene group or a substituted or unsubstituted $C_2$-$C_{50}$ divalent heterocyclic group including N, O or S as a heteroelement, Ar' is a substituted or unsubstituted $C_6$-$C_{50}$ aryl group or a substituted or unsubstituted $C_2$-$C_{50}$ heterocyclic group including N, O or S as a heteroelement, X is a substituent group selected from the following Structural Formulas,

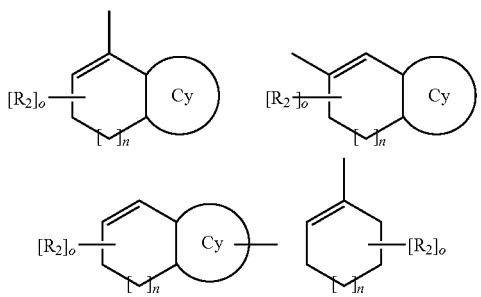

in the Structural Formulas, Cy is a substituted or unsubstituted $C_6$-$C_{50}$ aryl group or a substituted or unsubstituted $C_2$-$C_{50}$ heterocyclic group including N, O or S as a heteroelement, $R_2$ is selected from the group consisting of a substituted or unsubstituted $C_1$-$C_{40}$ alkyl group; a substituted or unsubstituted $C_1$-$C_{40}$ alkoxy group; a substituted or unsubstituted $C_2$-$C_{40}$ alkenyl group; a substituted or unsubstituted $C_6$-$C_{50}$ aryl group; a substituted or unsubstituted $C_6$-$C_{50}$ arylamine group; a substituted or unsubstituted $C_2$-$C_{50}$ heteroarylamine group including N, O or S as a heteroelement; a substituted or unsubstituted $C_2$-$C_{50}$ heterocyclic group including O, N or S as a heteroelement; a substituted amino group; a nitrile group; a nitro group; a halogen group; and an amine group, n is an integer of 0 to 5, O is an integer of 0 to 10, and in the case where O is 2 or more, $R_2$s may be the same as or different from each other, and in the case where l, m or p is 2 or more, Ar, Ar', or $R_1$ may be the same as or different from each other.

In the exemplary embodiment of the present invention, in Formula 1, in the case where X is the following Formula and CY is $C_6$ aryl, that is, a benzene cycle, n is preferably 1 or more and more preferably 1 or 2.

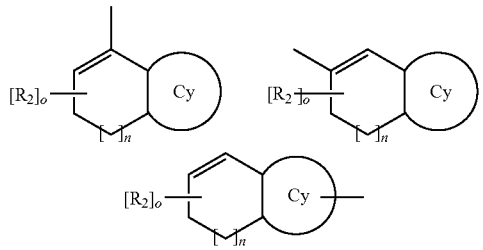

In the exemplary embodiment of the present invention, in Formula 1, in the case where X is the following Formula, it is preferable that $R_1$ is disposed at a 9 position of anthracene of Formula 1, and at least one Ar' is disposed at a 10 position of anthracene. In this case, at least one substituent group may be further disposed at another position of anthracene.

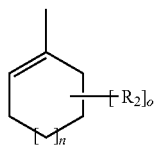

In the exemplary embodiment of the present invention, in Formula 1, in the case where X is the following Formula, p is an integer of 1 to 3, and Ar' is preferably a substituted or unsubstituted $C_6$-$C_{50}$ aryl group or a substituted or unsubstituted $C_2$-$C_{50}$ heterocyclic group including N as a heteroelement, and more preferably a substituted or unsubstituted $C_6$-$C_{50}$ aryl group.

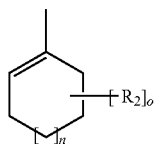

In Formula 1, it is more preferable that m is 0 or 1.

In Formula 1, in the case where p is 0, it is preferable that l is 2 to 4.

In the case where there is no specific description in Formula 1, the term "substituted or unsubstituted" means to be substituted or unsubstituted by one or more substituent groups that are selected from the group consisting of heavy hydrogen, a halogen group, an alkyl group, an alkenyl group, an alkoxy group, an aryl group, an arylalkyl group, an arylalkenyl group, a heterocycle 위에는 group, a carbazolyl group, a fluorenyl group, a nitrile group, and an acetylene group, but the term is not limited thereto.

In Formula 1, in the case where an alkyl group, an alkoxy group, an alkenyl group, an aryl group, an arylamine group, a heteroarylamine group, or a heterocyclic group is substituted, it is preferable that the group is substituted by one or more substituent groups selected from the group consisting of heavy hydrogen, a halogen group, an alkyl group, an alkenyl group, a substituted or unsubstituted alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted heterocyclic group, a nitrile group, and a substituted or unsubstituted acetylene group. In the case where the amino group is substituted, it is preferable that the group is substituted by one or more substituent groups selected from the group consisting of alkyl group, alkenyl group, substituted or unsubstituted aryl group, substituted or unsubstituted arylalkyl group, and substituted or unsubstituted arylalkenyl group.

In the case where there is no specific description in Formula 1, the alkyl group and alkoxy group have preferably 1 to 40 carbon atoms and more preferably 1 to 20 carbon atoms. In addition, the alkenyl group has preferably 2 to 40 carbon atoms and more preferably 2 to 20 carbon atoms. In addition, the aryl group has preferably 6 to 40 carbon atoms and more preferably 6 to 20 carbon atoms. In addition, the heterocyclic group has preferably 2 to 50 carbon atoms, more preferably 4 to 40 carbon atoms, and more preferably 4 to 20 carbon atoms. In addition, the arylamine group has preferably 6 to 60 carbon atoms and more preferably 6 to 24 carbon atoms. In addition, the heteroarylamine group has preferably 2 to 60 carbon atoms, preferably 4 to 40 carbon atoms, and more preferably 4 to 20 carbon atoms.

It is preferable that the compound represented by Formula 1 is represented by the following Formula 2-1 or Formula 2-2.

[Formula 2-1]

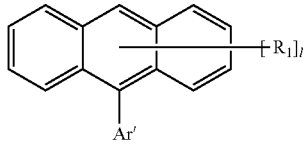

[Formula 2-2]

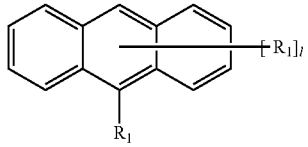

In Formula 2-1 and Formula 2-2, $R_1$ and Ar' are the same as the definitions of Formula 1, and in the case where $R_1$ is 2 or more, $R_1$ and Ar' may be the same as or different from each other, and l is an integer of 1 to 3.

In addition, it is preferable that the compound represented by Formula 1 is represented by the following Formula 3-1 or Formula 3-2.

[Formula 3-1]

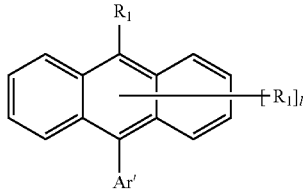

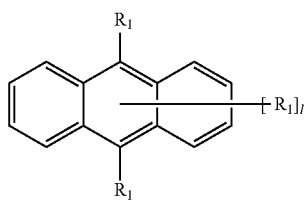
[Formula 3-2]

In Formula 3-1 and Formula 3-2, $R_1$ and Ar' are the same as the definitions of Formula 1, and in the case where $R_1$ is 2 or more, $R_1$ and Ar' may be the same as or different from each other, and l is an integer of 0 to 2.

In addition, it is preferable that the compound represented by Formula 1 is represented by any one of the following Formula 4-1 to Formula 4-4.

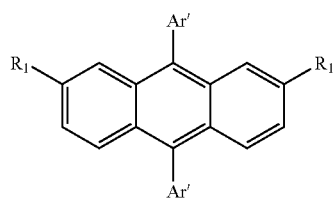
[Formula 4-1]

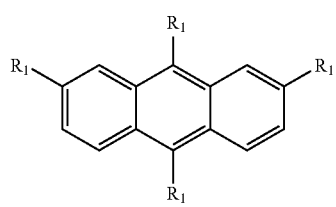
[Formula 4-2]

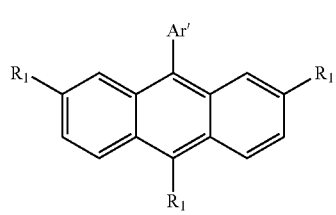
[Formula 4-3]

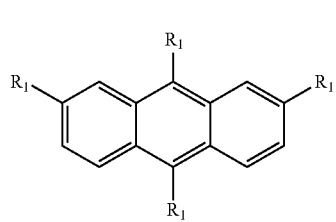
[Formula 4-4]

In Formula 4-1 to Formula 4-4, $R_1$s are the same as the definitions of Formula 1, and may be the same as or different from each other, and Ar's are the same as the definitions of Formula 1, and may be the same as or different from each other.

In addition, it is preferable that the compound represented by Formula 1 is represented by any one of the following Formula 5-1 to Formula 5-3.

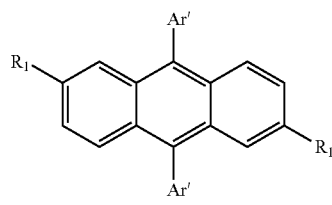
[Formula 5-1]

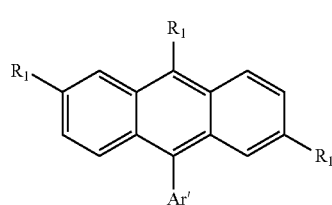
[Formula 5-2]

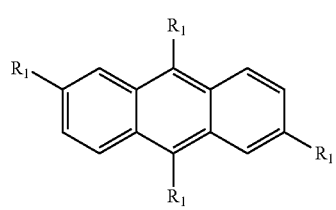
[Formula 5-3]

In Formula 5-1 to Formula 5-3, $R_1$s are the same as the definitions of Formula 1, and may be the same as or different from each other, and Ar's are the same as the definitions of Formula 1, and may be the same as or different from each other.

In addition, it is preferable that the compound represented by Formula 1 is represented by any one of the following Formula 6-1 to Formula 6-4.

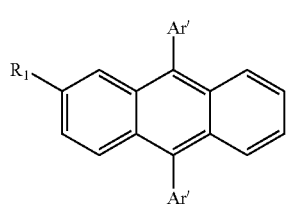
[Formula 6-1]

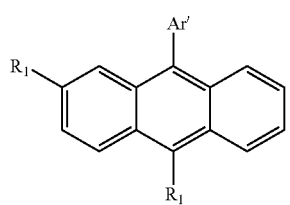
[Formula 6-2]

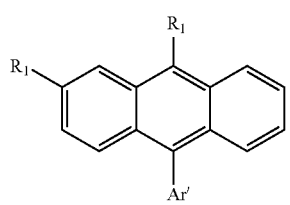
[Formula 6-3]

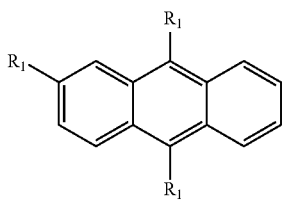
[Formula 6-4]

In Formula 6-1 to Formula 6-4, $R_1$s are the same as the definitions of Formula 1, and may be the same as or different from each other, and Ar's are the same as the definitions of Formula 1, and may be the same as or different from each other.

In addition, it is preferable that the compound represented by Formula 1 is represented by any one of the following Formula 7-1 to Formula 7-4.

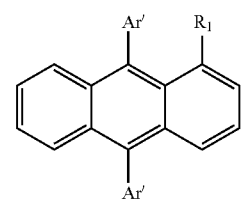
[Formula 7-1]

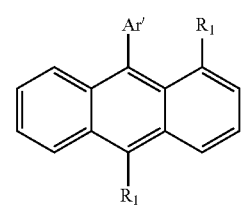
[Formula 7-2]

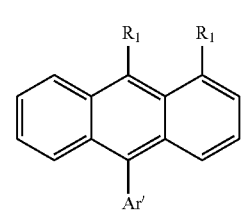
[Formula 7-3]

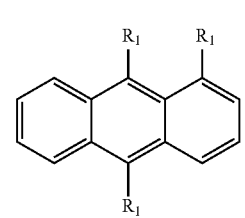
[Formula 7-4]

In Formula 7-1 to Formula 7-4, $R_1$s are the same as the definitions of Formula 1, and may be the same as or different from each other, and Ar's are the same as the definitions of Formula 1, and may be the same as or different from each other.

In addition, it is preferable that the compound represented by Formula 1 is represented by any one of the following Formula 8-1 to Formula 8-5.

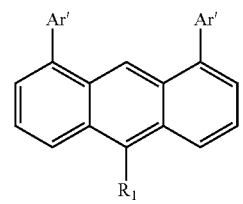
[Formula 8-1]

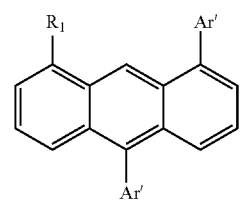
[Formula 8-2]

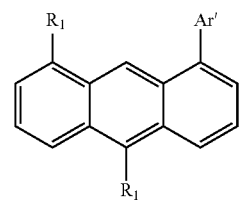
[Formula 8-3]

[Formula 8-4]

[Formula 8-5]

In Formula 8-1 to Formula 8-5, $R_1$s are the same as the definitions of Formula 1, and may be the same as or different from each other, and Ar's are the same as the definitions of Formula 1, and may be the same as or different from each other.

In the above Formulas, it is preferable that Ar is a $C_1$-$C_{10}$ alkyl group, a $C_6$-$C_{12}$ aryl group, a $C_2$-$C_{12}$ heterocyclic group including O, N or S as a heteroatom, a $C_6$-$C_{26}$ arylene group that is substituted or unsubstituted by a silyl group or a $C_1$-$C_{10}$ alkylsilyl group; or a $C_1$-$C_{10}$ alkyl group, a $C_6$-$C_{12}$ aryl group, a $C_2$-$C_{12}$ heterocyclic group including O, N or S as the heteroatom, and a $C_2$-$C_{26}$ divalent heterocyclic group that is substituted or unsubstituted by a silyl group or a $C_1$-$C_{10}$ alkylsilyl group and includes O, N or S as the heteroatom.

In addition, it is preferable that the arylene group in Ar is selected from the group consisting of a phenylene group, a naphthylene group, a biphenylene group, an anthracenylene group and the following Structural Formulas.

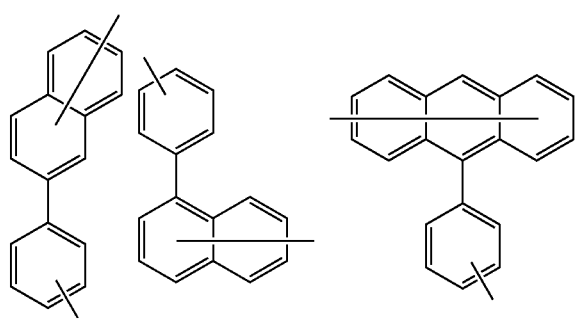

In the above Formulas, it is preferable that $R_2$ is a $C_1$-$C_{10}$ alkyl group; a $C_6$-$C_{26}$ aryl group that is substituted or unsubstituted by a $C_1$-$C_{10}$ alkyl group, a $C_6$-$C_{12}$ aryl group, a $C_2$-$C_{12}$ heterocyclic group that is substituted or unsubstituted by a $C_6$-$C_{12}$ aryl group and includes O, N or S as a heteroatom, a silyl group or a $C_1$-$C_{10}$ alkylsilyl group; or a $C_2$-$C_{26}$ heterocyclic group that is substituted or unsubstituted by a $C_1$-$C_{10}$ alkyl group, a $C_6$-$C_{12}$ aryl group, a $C_2$-$C_{12}$ heterocyclic group that is substituted or unsubstituted by a $C_6$-$C_{12}$ aryl group and includes O, N or S as a heteroatom, a silyl group or a $C_1$-$C_{10}$ alkylsilyl group and includes O, N or S as a heteroatom.

In the above Formulas, it is preferable that $R_1$ is selected from the group consisting of substituent groups represented by the following Structural Formulas, but $R_1$ is not limited thereto.

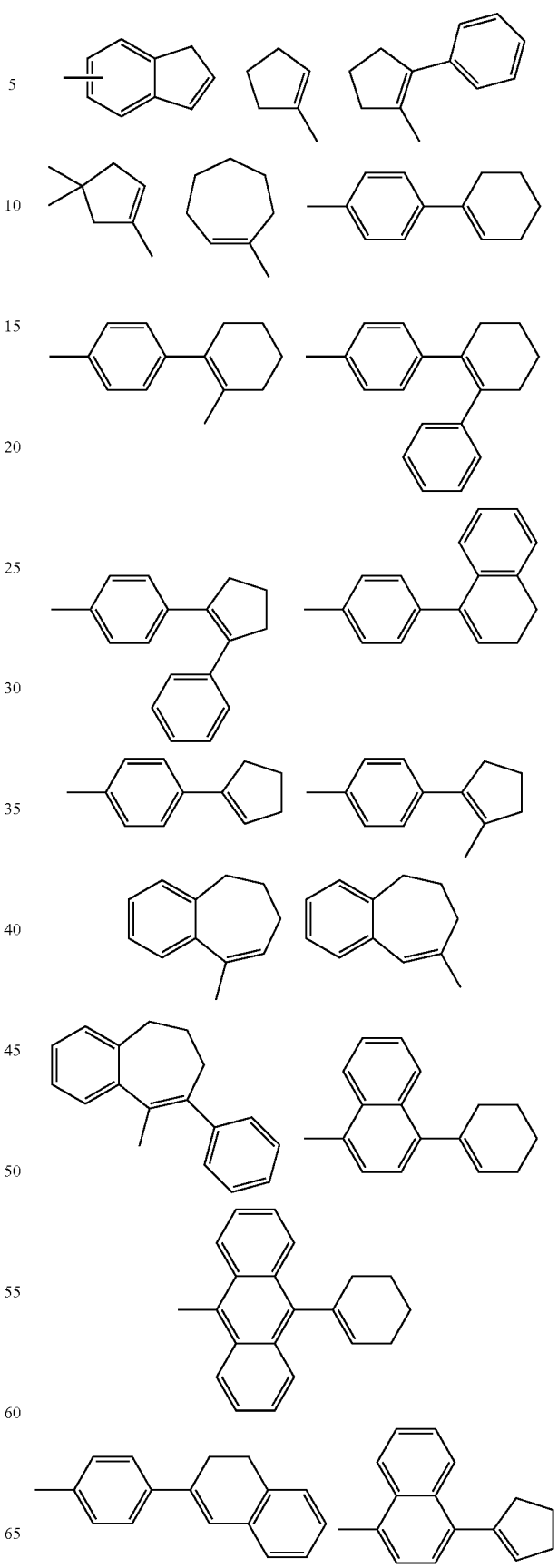

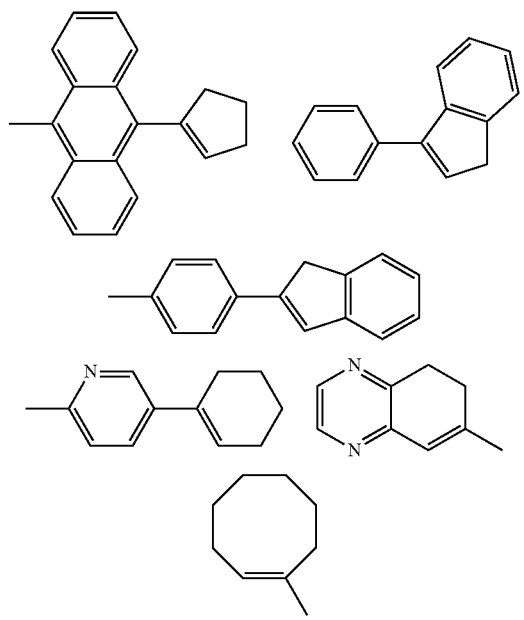

In the above Formulas, Ar' is preferably a $C_6$-$C_{26}$ aryl group that is substituted or unsubstituted by a $C_1$-$C_{10}$ alkyl group, a $C_6$-$C_{12}$ aryl group, a $C_2$-$C_{12}$ heterocyclic group that is substituted or unsubstituted by a $C_6$-$C_{12}$ aryl group and includes O, N or S as a heteroatom, a silyl group or a $C_1$-$C_{10}$ alkylsilyl group; or a $C_2$-$C_{26}$ heterocyclic group that is substituted or unsubstituted by a $C_1$-$C_{10}$ alkyl group, a $C_6$-$C_{12}$ aryl group, a $C_2$-$C_{12}$ heterocyclic group that is substituted or unsubstituted by a $C_6$-$C_{12}$ aryl group and includes O, N or S as a heteroatom, a silyl group or a $C_1$-$C_{10}$ alkylsilyl group and includes O, N or S as a heteroatom, and is more preferably selected from the group consisting of the substituent groups represented by the following Structural Formulas, but is not limited thereto.

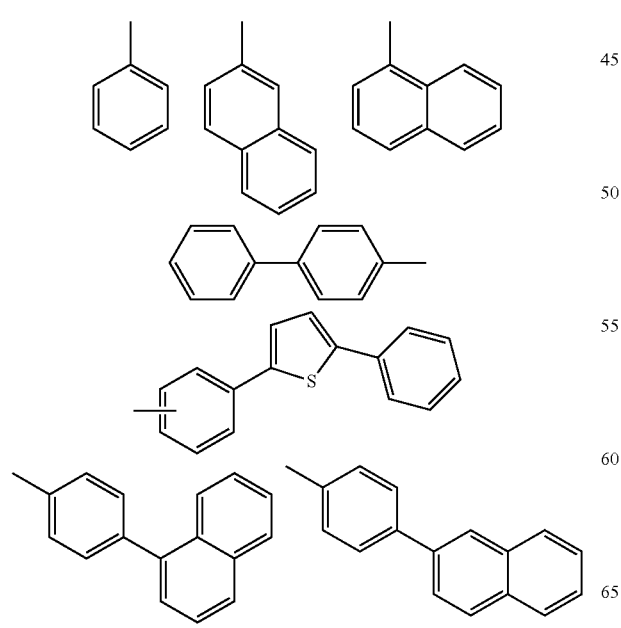

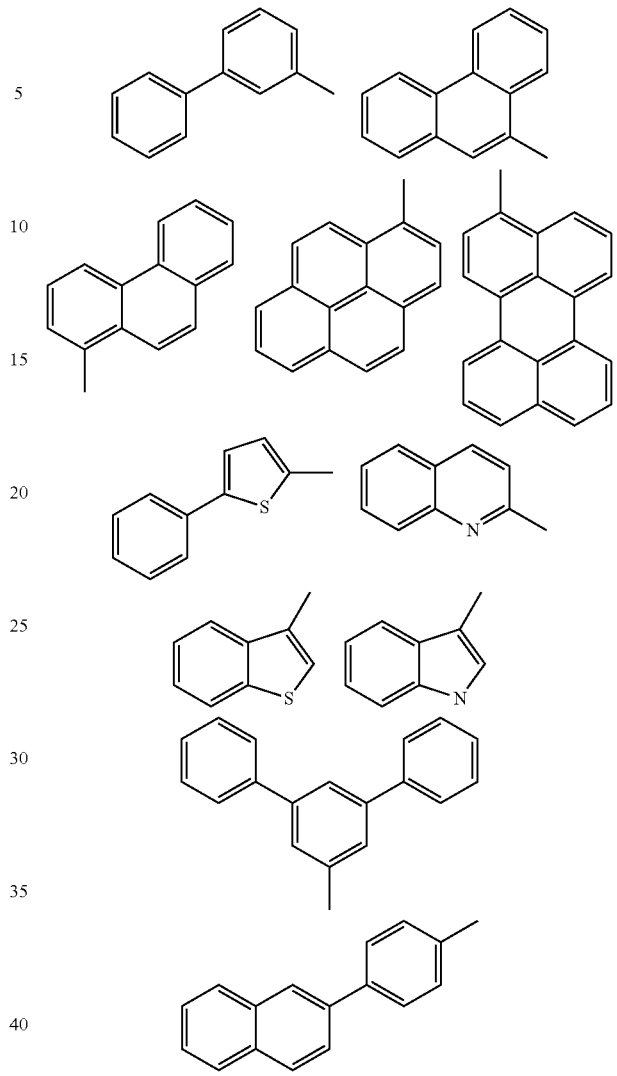

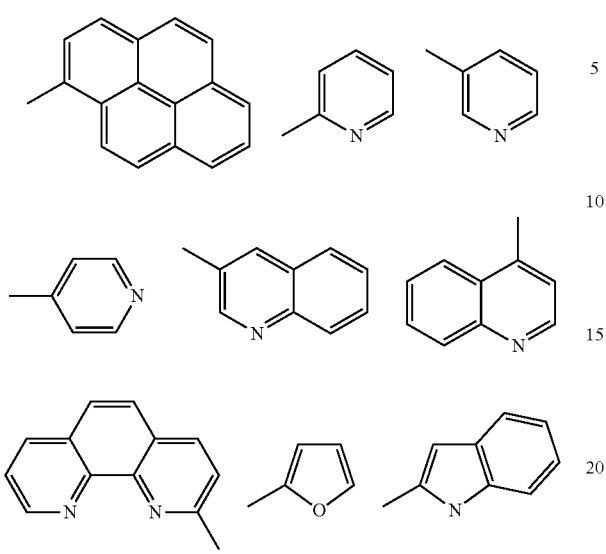
It is preferable that detailed examples of the compound according to the exemplary embodiment of the present invention are selected from the following compounds 1 to 88, but are not limited thereto.
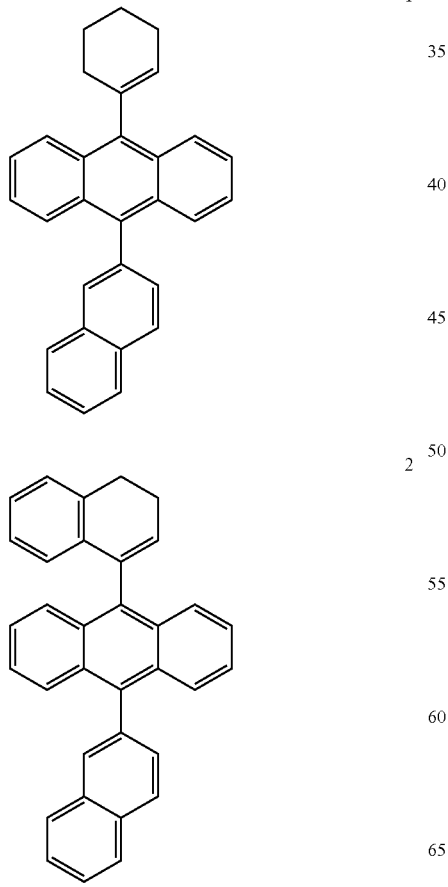
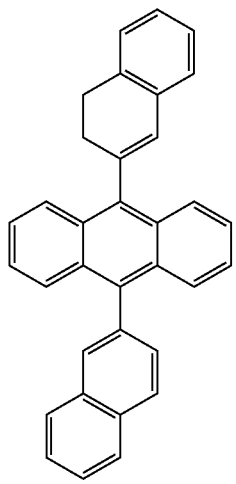
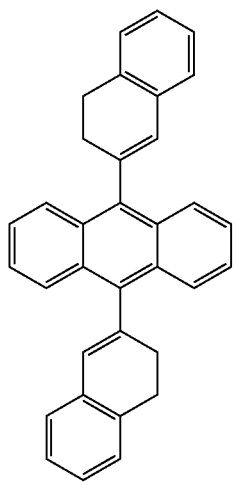
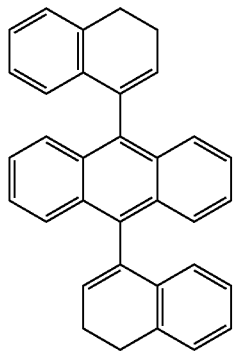

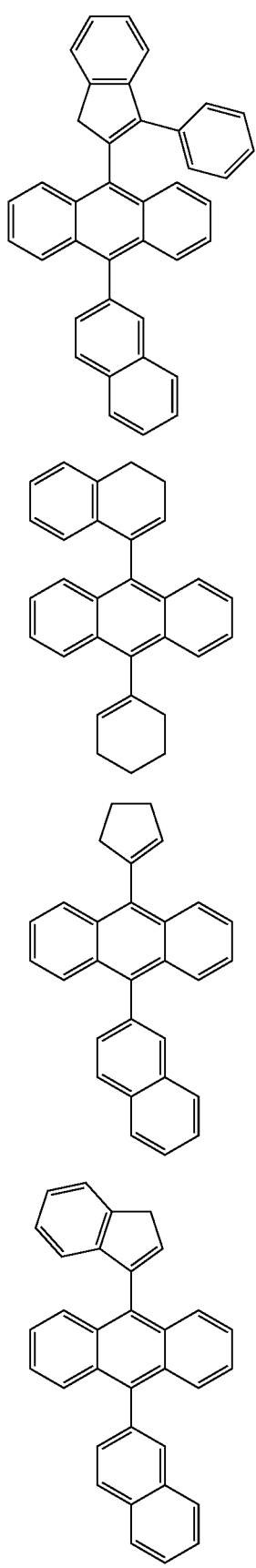
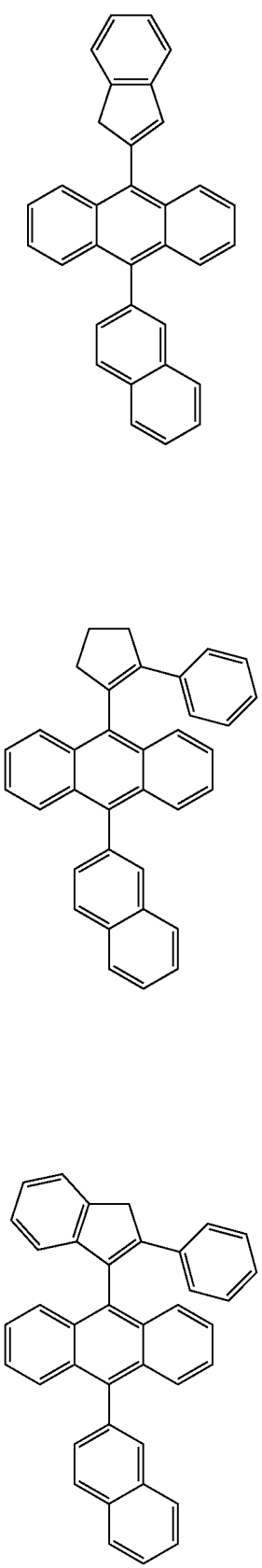

13
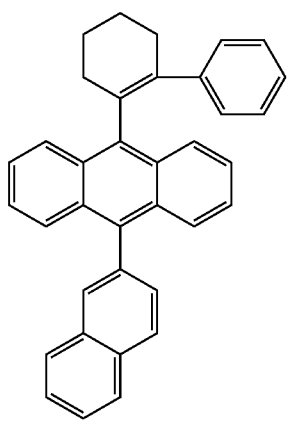
14
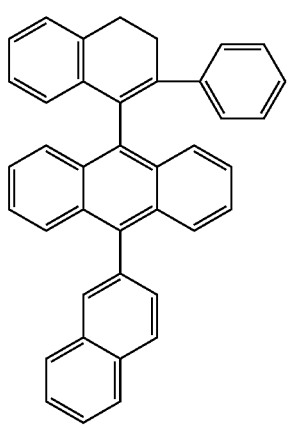
15
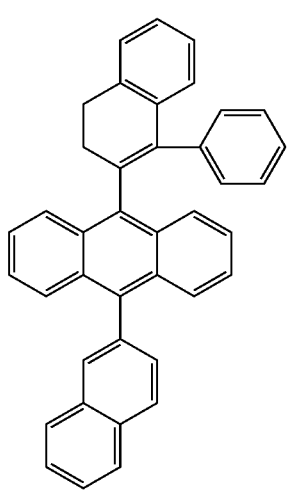
16
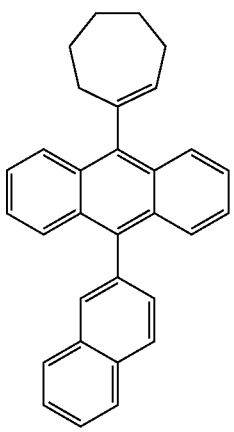
17
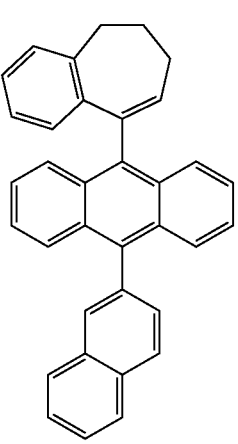
18
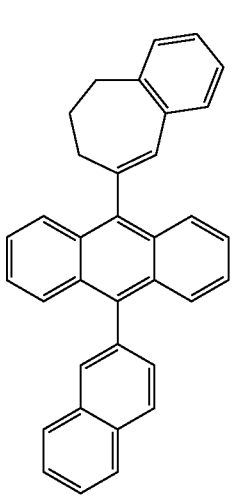

19
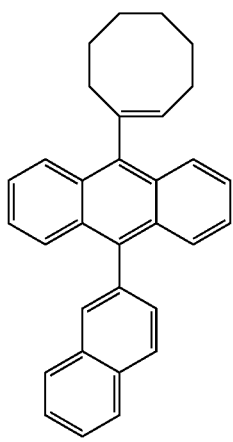
20
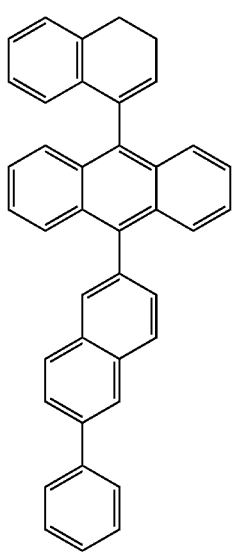
21
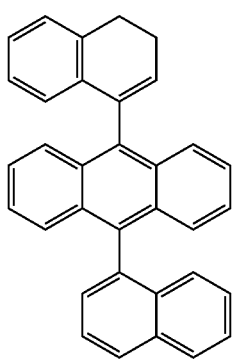
22
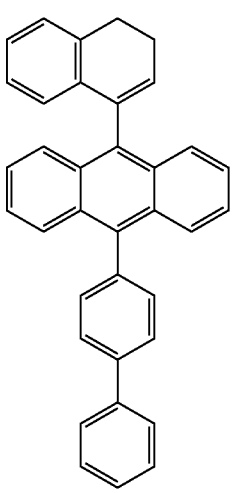
23
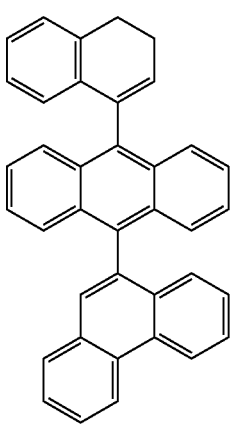
24
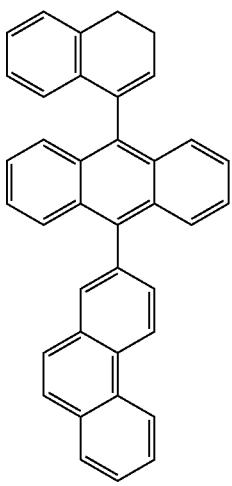

25
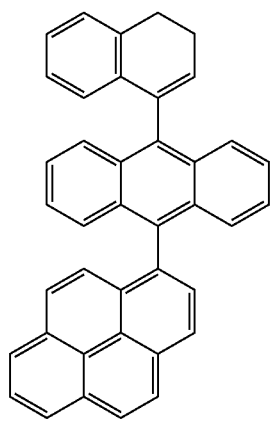
26
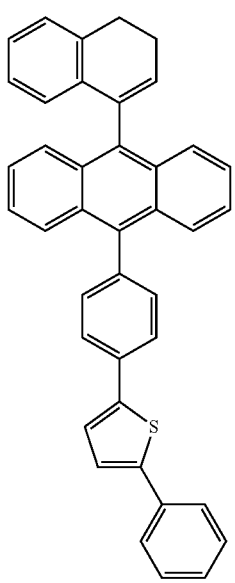
27
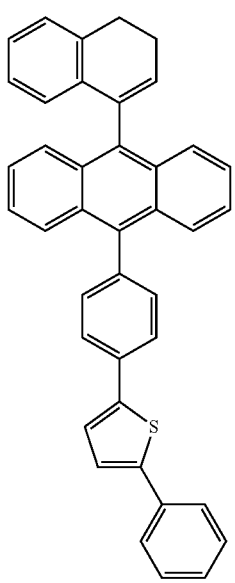
28
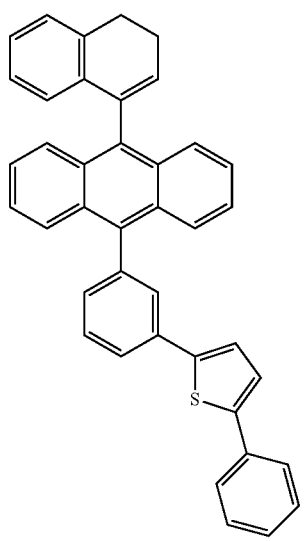
29
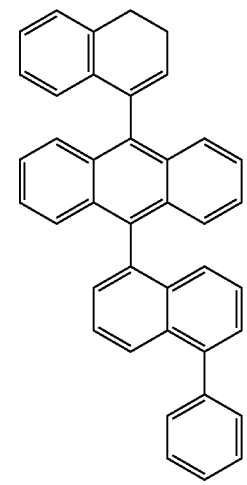
30
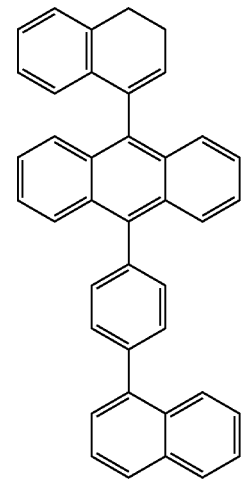

-continued
31
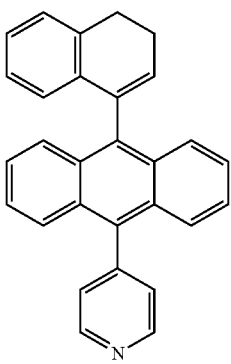
32
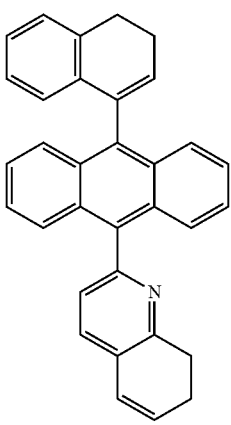
33
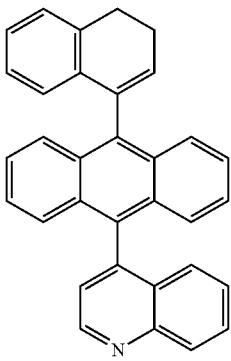
34
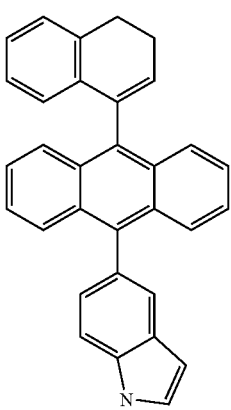
-continued
35
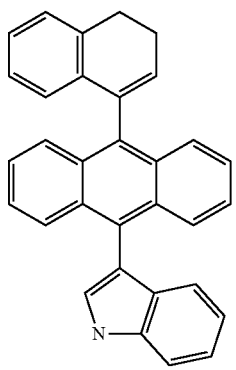
36
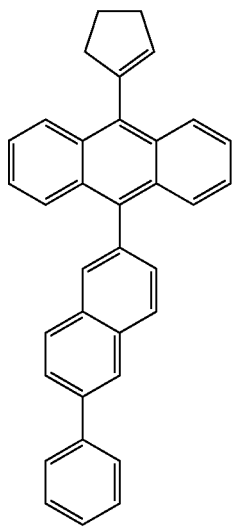
37
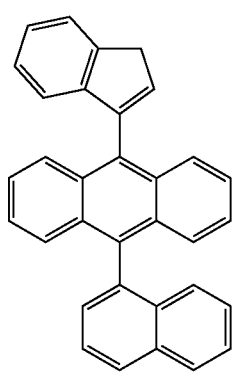

38
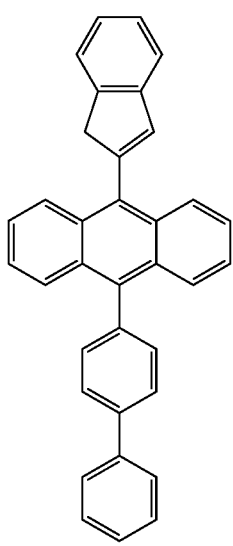
39
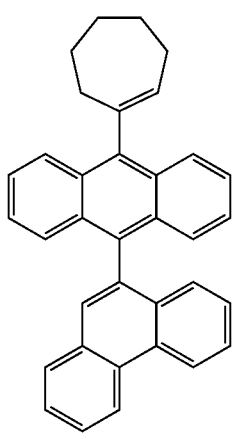
40
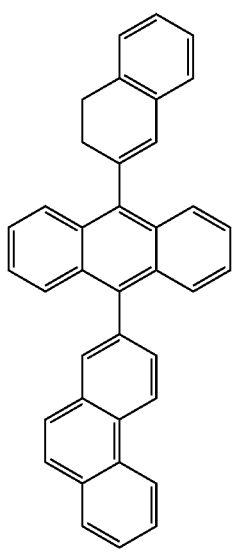
41
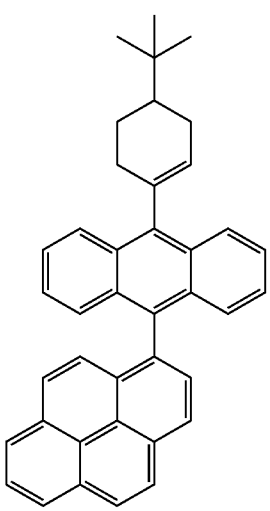
42
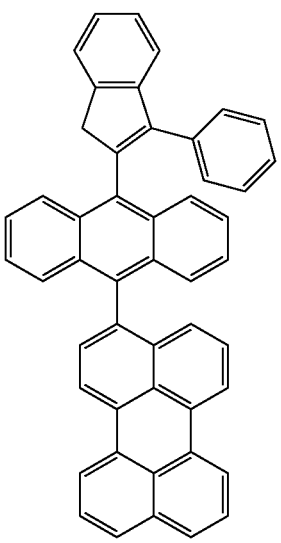
43
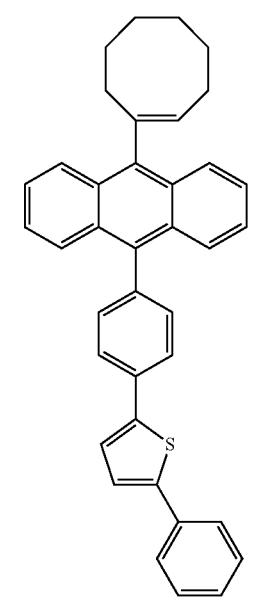

44
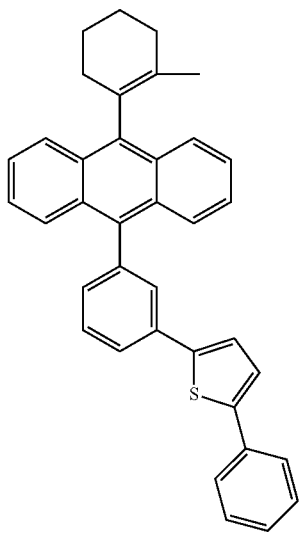
45
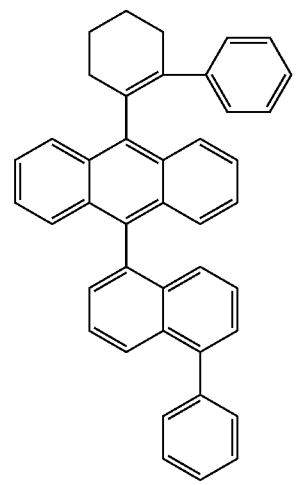
46
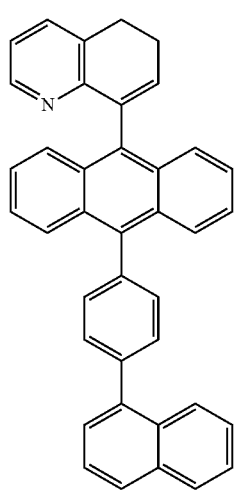
47
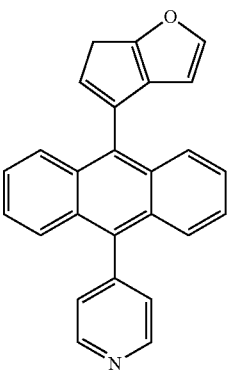
48
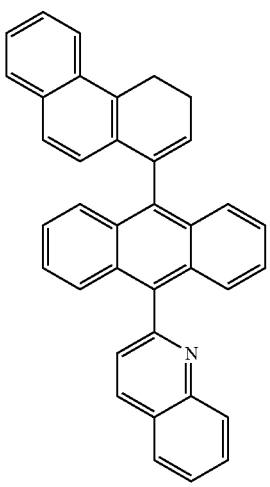
49
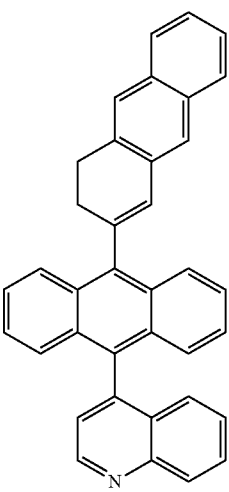

| 31 | 32 |
|---|---|
| -continued | -continued |
| 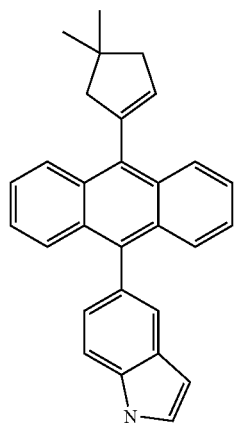 50 | 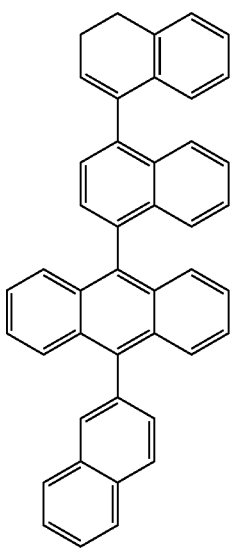 53 |
| 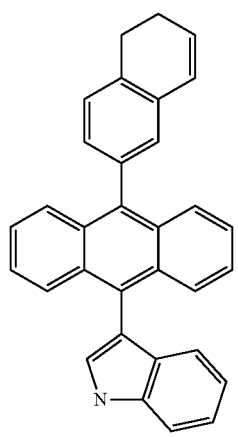 51 | 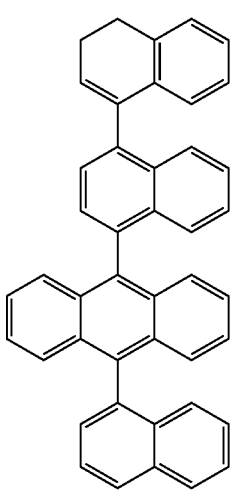 54 |
| 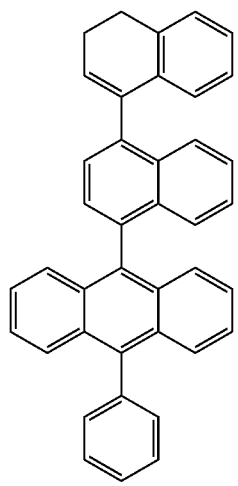 52 | 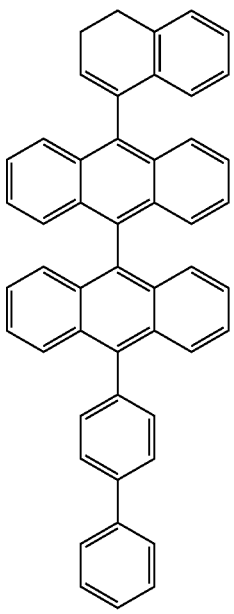 55 |

56
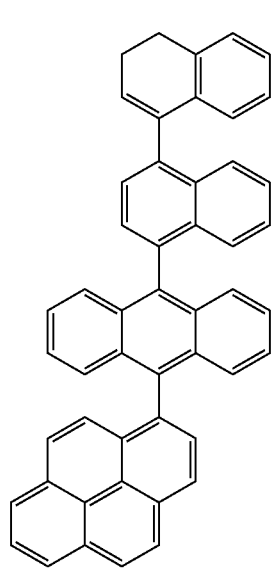
58
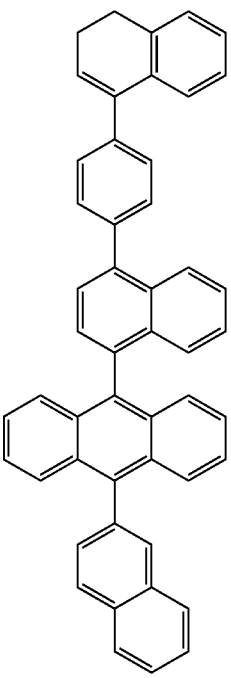
57
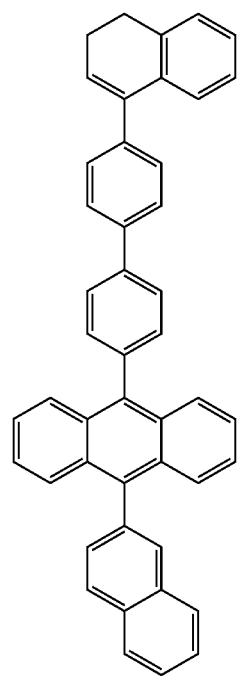
59
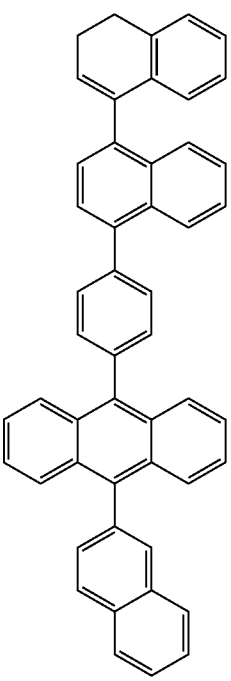

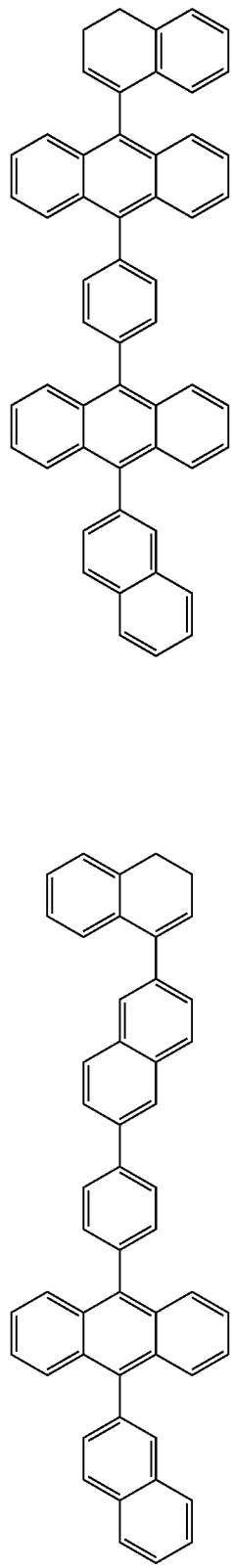
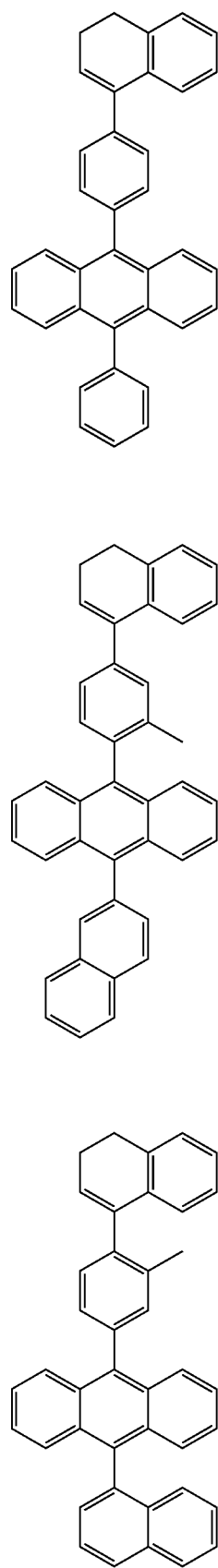

65
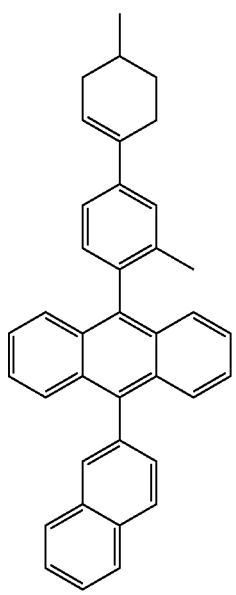
66
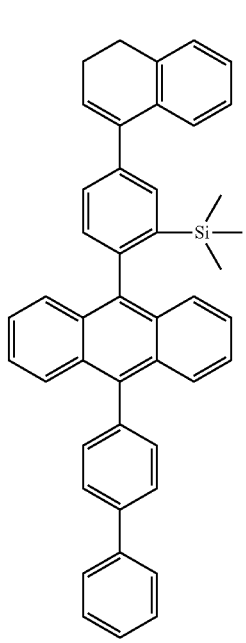
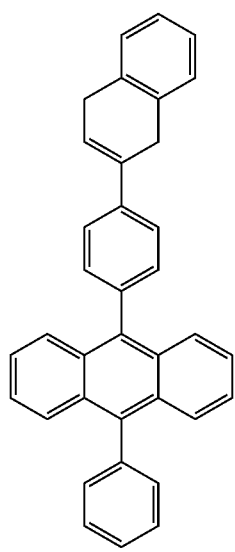
67
68
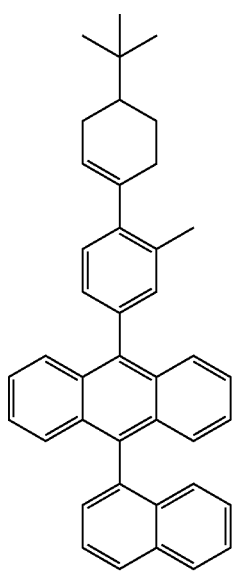

69
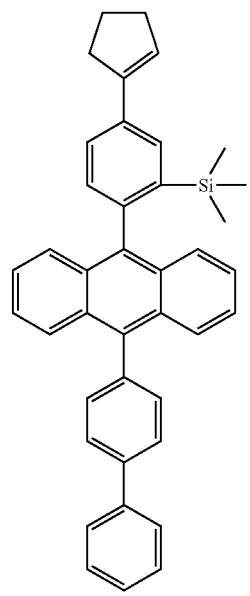
70
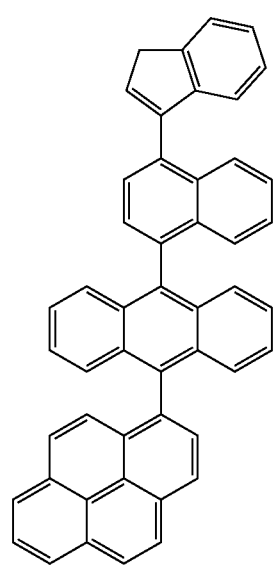
71
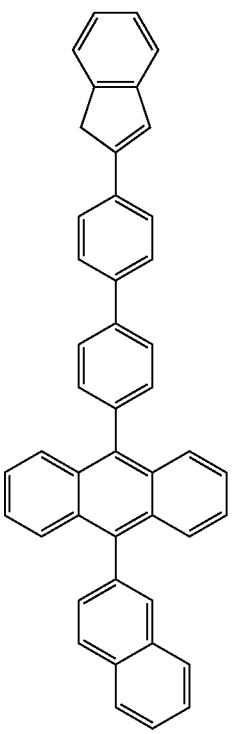
72
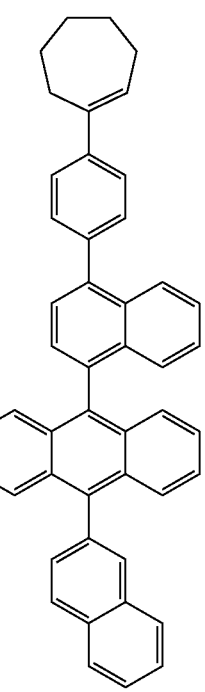

73
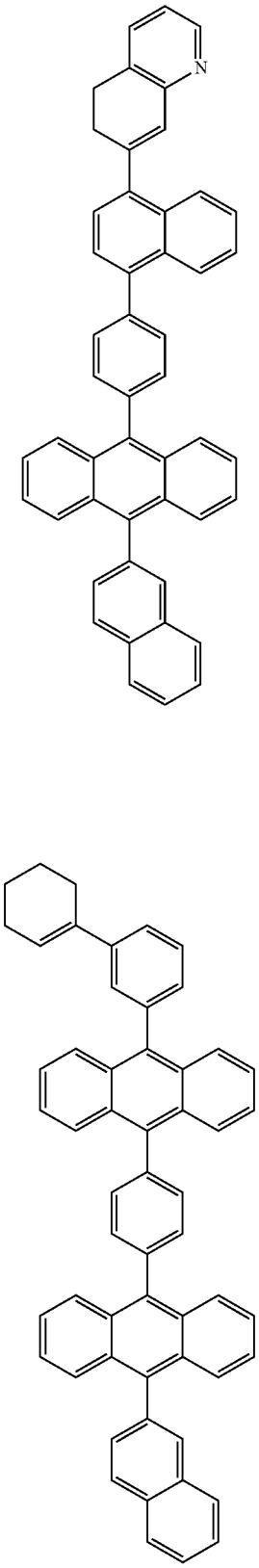
74
75
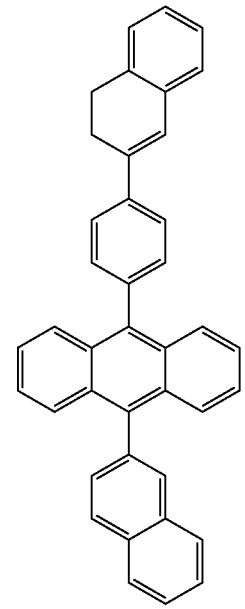
76
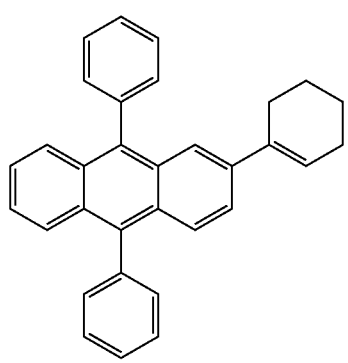
77
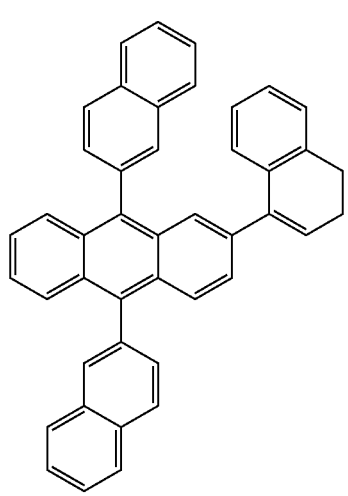

78
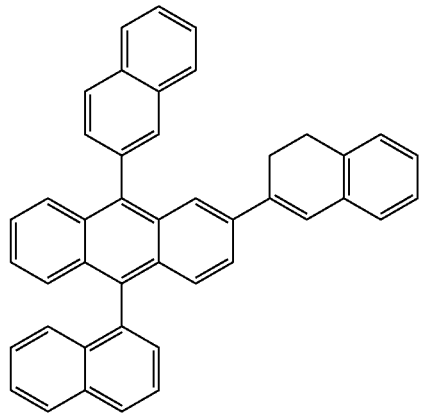
79
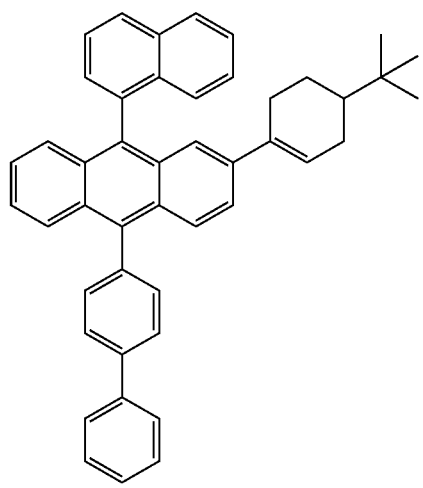
80
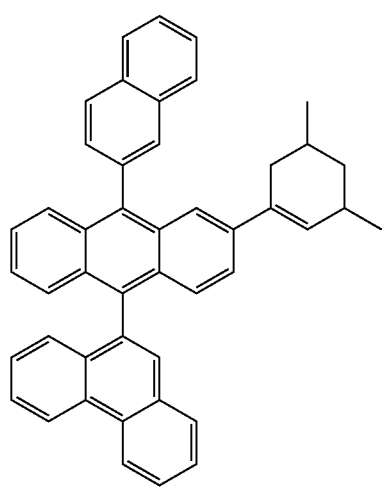
81
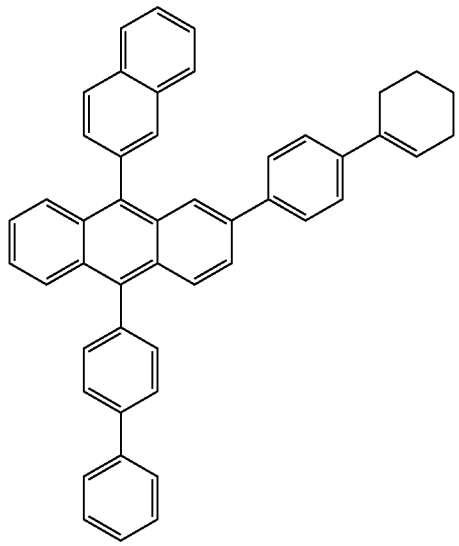
82
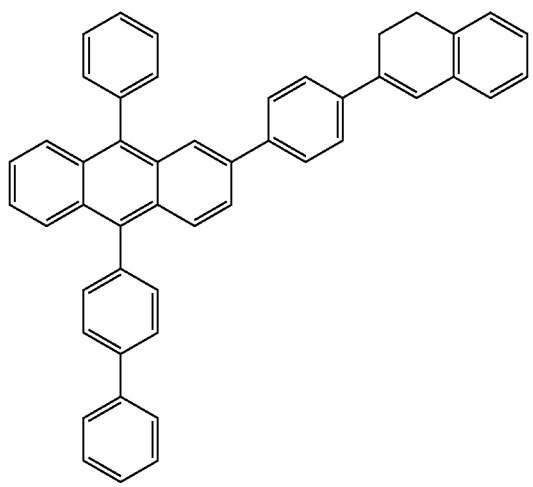
83
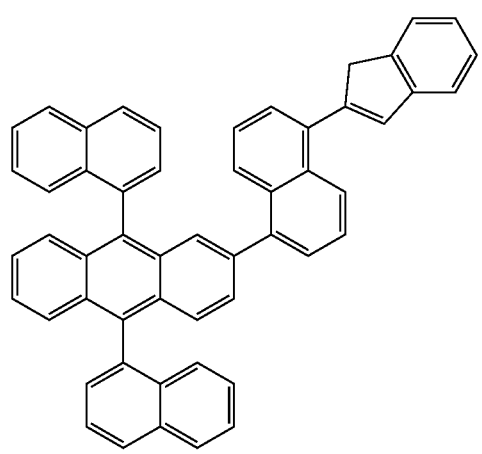

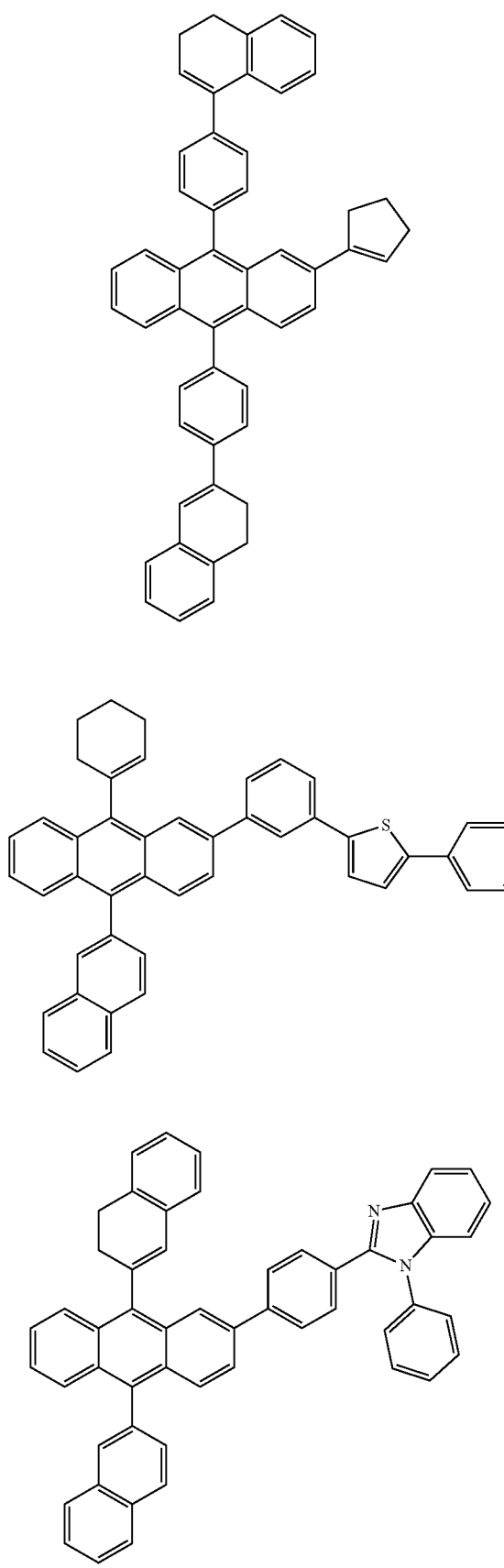
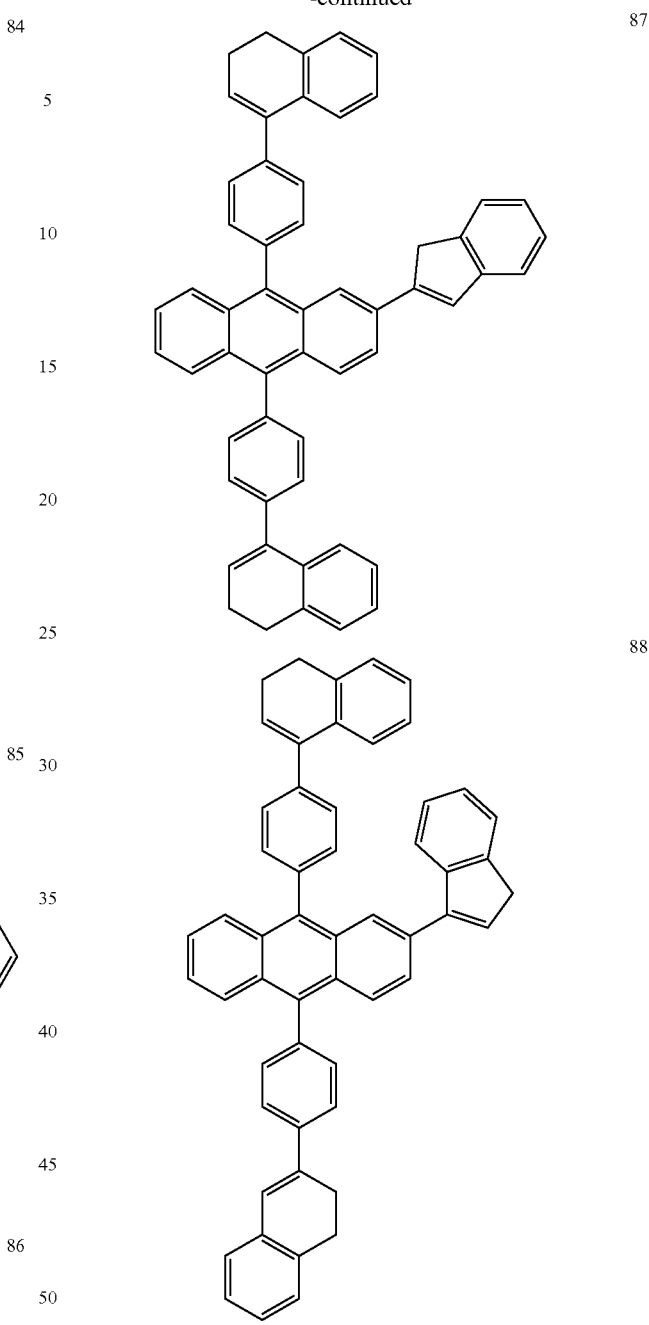

The compound according to the exemplary embodiment of the present invention may be manufactured by reacting a boronic acid compound of an anthracene derivative and a halide of a cycloalkene derivative with each other. In this case, a reaction condition known in the art may be used. For example, the boronic acid compound of the anthracene derivative and the halide of the cycloalkene derivative may be reacted with each other by adding a solvent such as water and THF in the presence of tetrakistriphenylphosphinpalladium and potassium phosphate.

A second aspect of the present invention relates to an organic electronic device which includes a first electrode, a second electrode, and one or more organic material layers that are disposed between the first electrode and the second electrode, wherein one or more layers of the organic material layers include the above compound.

Herein, the organic material layer may include an electron or hole injection layer and an electron or hole transport layer, and the electron or hole injection layer and the electron or hole transport layer may include the above compound.

In addition, the organic material layer may include a light emitting layer, and the light emitting layer may include the above compound.

In this case, it is preferable that the organic electronic device is selected from the group consisting of an organic light emitting diode, an organic solar cell, an organic photoconductor (OPC), and an organic transistor.

The compound according to the exemplary embodiment of the present invention may be formed to an organic material layer by a vacuum deposition method and a solution coating method when the organic electronic device is manufactured. Herein, illustrative, but non-limiting, examples of the solution coating process include a spin coating process, a dip coating process, an inkjet printing process, a screen printing process, a spray process, and a roll coating process.

The organic electronic device of the present invention may be produced using materials and methods known in the art, except that at least one layer of organic material layers include the compound of the present invention, that is, the compound of Formula 1.

The organic material layer of the organic electronic device according to the present invention may have a single layer structure, or a multilayered structure in which two or more organic material layers are layered. For example, the organic electronic device according to the exemplary embodiment of the present invention may have a structure including a hole injection layer, a hole transport layer, a light emitting layer, an electron transport layer, and an electron injection layer as the organic material layer. However, the structure of the organic electronic device is not limited thereto, and may include the smaller number of organic material layers.

Furthermore, the organic electronic device of the present invention may be produced, for example, by sequentially layering a first electrode, organic material layers, and a second electrode on a substrate. In this case, a physical vapor deposition (PVD) method, such as a sputtering method or an e-beam evaporation method, may be used, but the method is not limited thereto.

As the anode material, in general, it is preferable to use the material having a large work function so as to smoothly perform hole injection into the organic material layer. As detailed examples of the anode material that can be used in the present invention, there are metal such as vanadium, chrome, copper, zinc, gold and the like or an alloy thereof; metal oxides such as zinc oxides, indium oxides, indium tin oxides (ITO), indium zinc oxides (IZO) and the like; a combination of metal and oxides such as ZnO:Al or $SnO_2$:Sb; and conductive polymers such as poly(3-methylthiophene), poly[3,4-(ethylene-1,2-dioxy)thiophene] (PEDT), polypyrrole, and polyaniline, but it is not limited thereto.

As the cathode material, in general, it is preferable to use the material having a small work function so as to smoothly perform electron injection into the organic material layer. As detailed examples of the cathode material, there are metal such as magnesium, calcium, sodium, potassium, titanium, indium, yttrium, lithium, gadolinium, aluminum, silver, tin, and lead or an alloy thereof; and a multilayered structure material such as LiF/Al or $LiO_2$/Al, but it is not limited thereto.

The hole injection material is a material that can receive holes well from the anode at a low voltage, and it is preferable that the highest occupied molecular orbital (HOMO) of the hole injection material is a value between the work function of the anode material and the HOMO of the surrounding organic material layer. As detailed examples of the hole injecting material, there are organic materials of metal porphyrin, oligothiophene, and arylamine series, organic materials of hexanitrile hexaazatriphenylene, and quinacridone series, organic materials of perylene series, and conductive polymers of anthraquinone, polyaniline, and polythiophene series, but it is not limited thereto.

The hole transport material is a material that can receive the holes from the anode or the hole injection layer and transfer the received holes to the light emitting layer, and it is preferable to use the material having the large mobility to the holes. As detailed examples thereof, there are arylamine-based organic material, a conductive polymer, and a block copolymer in which a conjugate portion and a non-conjugate portion are simultaneously included, but it is not limited thereto.

The light emitting material is a material that receives the holes and the electrons from the hole transport layer and the electron transport layer, respectively, and combines them, such that light at a range of visible rays is emitted, and it is preferable to use the material having excellent photon efficiency to fluorescence or phosphorescence. As detailed examples thereof, there are a 8-hydroxy-quinoline aluminum complex ($Alq_3$); a carbazole-based compound; a dimerized styryl compound; BAlq; 10-hydroxybenzoquinoline-metal compound; a benzoxazole, benzthiazole, and benzimidazole-based compound; a poly(p-phenylenevinylene) (PPV)-based polymer; a spiro compound; polyfluorene, lubrene, and the like, but it is not limited thereto.

The electron transport material is a material that can receive the electrons well from the cathode and transfer the received electrons to the light emitting layer, and it is preferable to use the material having the large mobility to the electrons. As detailed examples thereof, there are a 8-hydroxyquinoline Al complex; a complex including $Alq_3$; an organic radical compound; a hydroxyflavone-metal complex and the like, but it is not limited thereto.

The organic light emitting diode according to the present invention may be a top emission type, a bottom emission type, or a both dual emission type according to the used material.

The compound according to the present invention may be operated even in an organic electronic device such as an organic solar cell, an organic photoconductor, and an organic transistor, in a principle similar to a principle applied to the organic light emitting diode.

Mode for Invention

The method for manufacturing the compound represented by Formula 1 and the manufacturing of an organic electronic device using the same will be described in detail in Preparation Examples and Examples. However, the Preparation Examples and Examples are set forth to illustrate the present invention, but the scope of the present invention is not limited thereto.

PREPARATION EXAMPLE

Preparation Example 1

Synthesis of Compound A

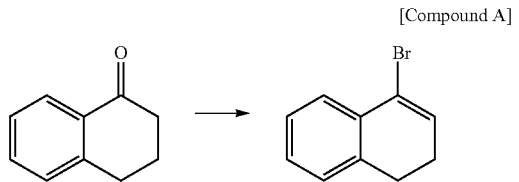 [SMILES: O=C1CCCc2ccccc21 ; BrC1=CCCc2ccccc21]

[Compound A]

Triphenylphosphite [(PhO)₃P] (18.5 mL, 70 mmol) was put into 200 mL of dichloromethane anhydride and cooled to −78° C. Under the nitrogen atmosphere, bromine (4 mL, 77 mmol) was slowly put. After that, trimethylamine anhydride (12 mL, 84 mmol) and tetrarone (9.36 g, 64 mmol) were put and heated for 18 hours to normal temperature with agitation. After that, 12.8 g of compound A was obtained at a yield of 96% by heating for about 2 hours, refluxing, and purifying using a chromatography. [M+]=208

Preparation Example 2

Synthesis of Compound 2

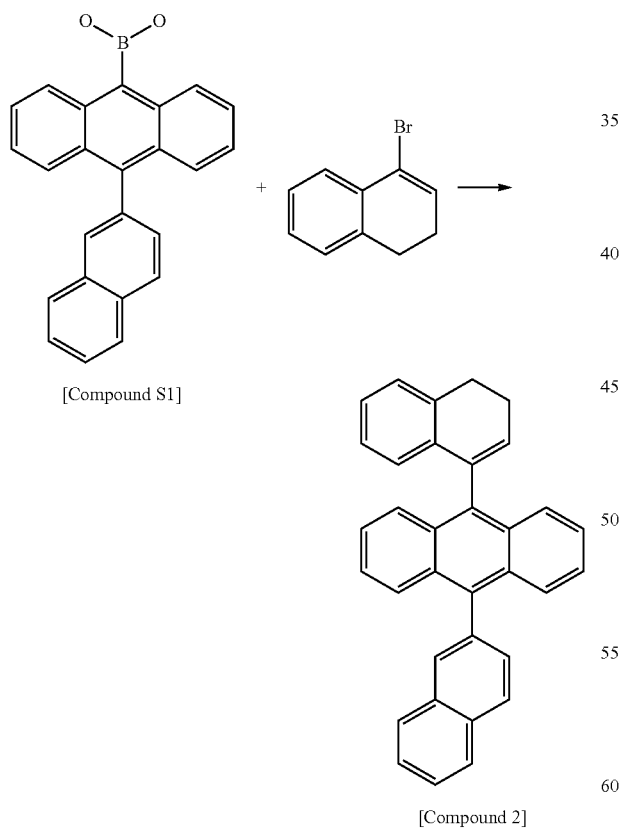

4 g of compound S1 (11.4 mmol), 2.4 g of compound A (11.4 mmol), 265 mg of tetrakistriphenylphosphinpalladium (Pd[PPh₃]₄, 0.229 mmol), and 4.87 g of potassium phosphate (K₃PO₄, 22.9 mmol) were put into 100 mL of water and 100 ml of THF, and refluxed and agitated. After 18 hours, the temperature was decreased to normal temperature, and the organic layer was separated. 3.08 g of compound 2 was obtained at a yield of 62% by removing the solvent and recrystallizing the generated solid in chloroform/methanol. [M+H]=433

Preparation Example 3

Synthesis of Compound 77

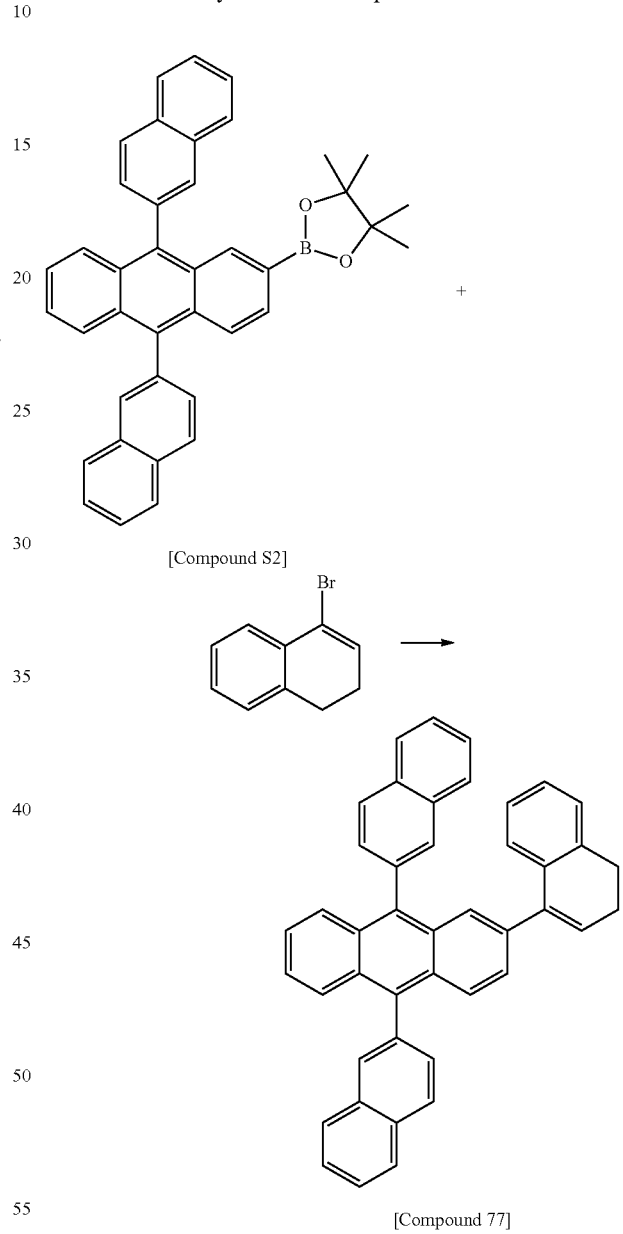

4 g of compound S2 (7.2 mmol), 1.65 g of compound A (7.9 mmol), 166 mg of tetrakistriphenylphosphinpalladium (Pd [PPh₃]₄, 0.143 mmol), and 3.04 g of potassium phosphate (K₃PO₄, 14.3 mmol) were put into 100 mL of water and 100 ml of THF, and refluxed and agitated. After 18 hours, the temperature was decreased to normal temperature, and the organic layer was separated. 3.6 g of compound 77 was obtained at a yield of 89% by removing the solvent and recrystallizing the generated solid in chloroform/methanol. [M+H]=559

Preparation Example 4

Synthesis of Compound C

The following preparation was implemented according to the method disclosed in Korean Unexamined Patent Application Publication No. 10-2007-0043664.

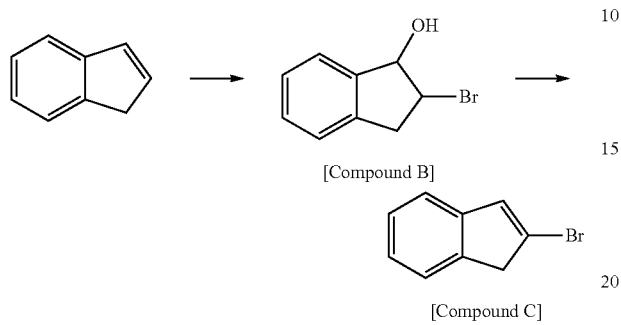

Indene (259 mmol, 30 g) and distilled water (9 mL) were put into dimethyl sulfoxide (DMSO, 90 mL), the temperature was decreased to 0° C., and N-bromosuccinimide (NBS, 263 mmol, 46.9 g) was slowly added thereto. The temperature of this solution was increased to normal temperature, and the solution was agitated for 12 hours. After that, after the reaction was finished by distilled water, the organic layer was extracted with diethyl ether, and moisture was removed by anhydrous magnesium sulfate. After the filtration under reduced pressure, compound B (38.9 g, 72%) was obtained by removing the solvent by reducing the pressure of the filtered solution and recrystallizing the solution by hexane.

14.3 g of compound B and p-toluenesulfonic acid (p-TsOH, 2.6 mmol, 0.5 g) were dissolved in 60 mL of toluene, and agitated and heated for 24 hours while water was removed by using the Tin-Stock method. Compound C (7.8 g, 60%) was obtained by decreasing the temperature of the solution to normal temperature and using the fractionation method.

[M]+=194

Preparation Example 5

Synthesis of Compound 10

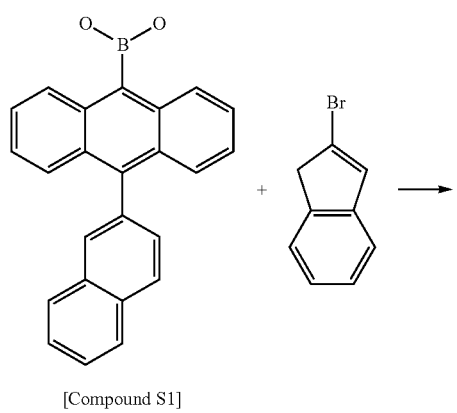

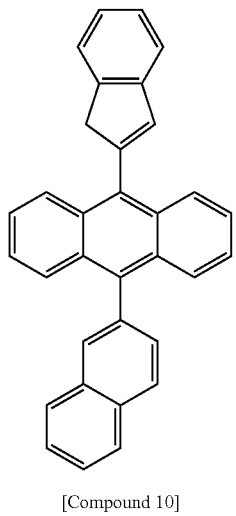

4 g of compound S1 (11.4 mmol), 2.69 g of compound A (13.8 mmol), 265 mg of tetrakistriphenylphosphinpalladium (Pd[PPh$_3$]$_4$, 0.229 mmol), and 4.87 g of potassium phosphate (K$_3$PO$_4$, 22.9 mmol) were put into 100 mL of water and 100 ml of THF, and refluxed and agitated. After 18 hours, the temperature was decreased to normal temperature, and the organic layer was separated. 4 g of compound 10 was obtained at a yield of 84% by removing the solvent and recrystallizing the generated solid in chloroform/methanol.
[M+H]=419

Experimental Example 1

A glass substrate on which a thin film of indium tin oxide (ITO) was coated to a thickness of 1500 Å was immersed in distilled water having a detergent dissolved therein and washed with ultrasonic waves. In this case, the detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was subsequently carried out by using solvents such as isopropyl alcohol, acetone, and methanol, and the resultant product was dried and transported to the plasma washing machine. The substrate was washed by using the oxygen plasma for 5 min, and the substrate was transported to the vacuum deposition machine.

On the ITO transparent electrode thus prepared, hexanitrile hexaazatriphenylene was deposited to thicknesses of 500 Å by heating under the vacuum to form a hole injecting layer. After NPB (400 Å) that was the material transporting the holes was deposited under the vacuum state thereon, compound 2 as the host and the dopant D1 compound were deposited under the vacuum state in a thickness of 300 Å as a light emitting layer.

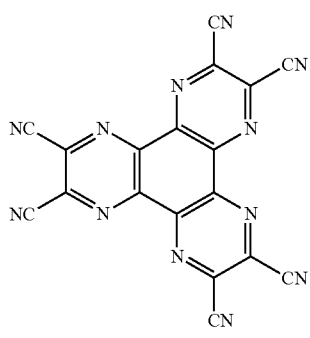

[hexanitrile hexaazatriphenylene]

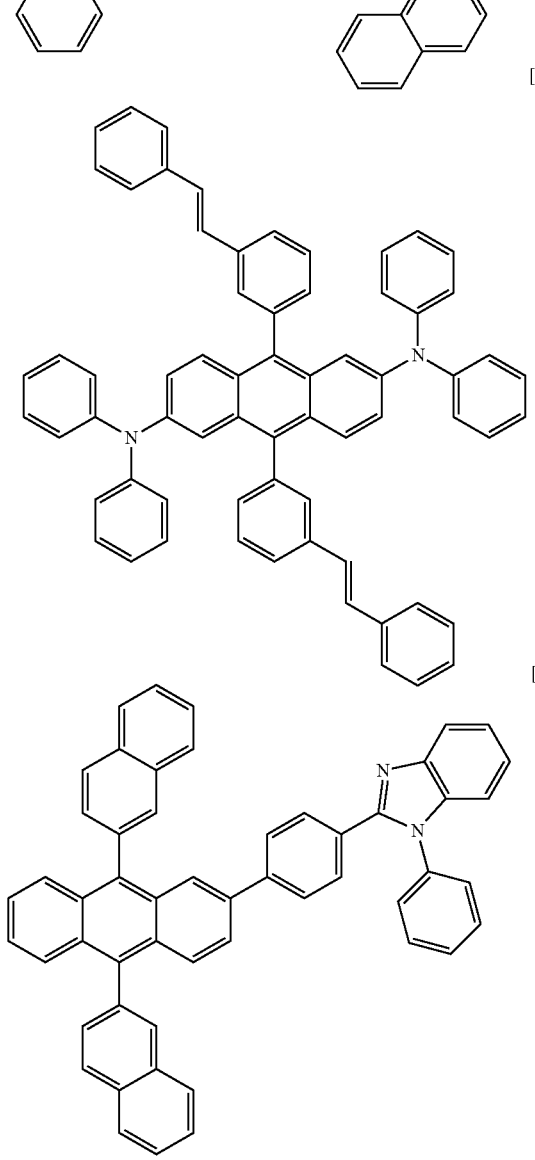

[NPB]

[D1]

[E1]

On the light emitting layer, the electron injection and transport layers were formed by depositing μl under the vacuum state in a thickness of 200 Å on the light emitting layer. On the electron injection and transport layer, lithium fluoride (LiF) in a thickness of 12 Å and aluminum in a thickness of 2000 Å were subsequently deposited to form a cathode.

Experimental Example 2

The experiment was performed in the same manner as Experimental Example 1, except that compound 77 was deposited instead of compound 2.

Experimental Example 3

The experiment was performed in the same manner as Experimental Example 1, except that compound 10 was deposited instead of compound 2.

In the above process, the deposition speed of the organic substance was maintained at 1 Å/sec, the deposition speed of lithium fluoride was maintained at 0.2 Å/sec, and the deposition speed of aluminum was maintained at 3 to 7 Å/sec.

Comparative Example

The experiment was performed in the same manner as Experimental Example 1, except that the following compound [H1] was used instead of compound 2.

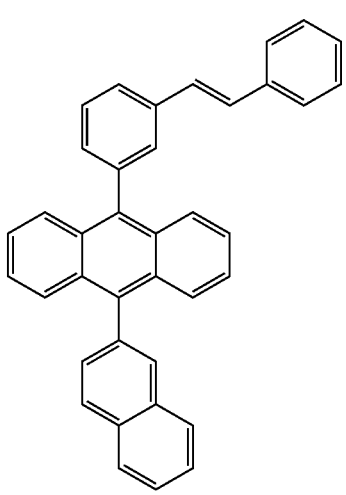

[H1]

The results of experiments through the Experimental Examples and Comparative Example are described in the following Table 1.

The measurement was performed at the current density of 50 mA/cm$^2$, and comparison and evaluation were performed in respect to a material having general noncycle alkene instead of known cycloalkene. Entirely, it can be seen that the compound including cycloalkene has a similar light emitting efficiency and a low voltage characteristic.

TABLE 1

| Exp. Example 50 mA/cm² | Host material | Dopant material | Voltage (V) | Current efficiency (cd/A) | Power efficiency (1 m/W) | Color coordinate (x, y) |
| --- | --- | --- | --- | --- | --- | --- |
| Exp. Example 1 | 2 | D1 | 6.04 | 26.04 | 13.54 | (0.312, 0.651) |
| Exp. Example 2 | 77 | D1 | 6.20 | 26.69 | 13.53 | (0.312, 0.649) |
| Exp. Example 3 | 10 | D1 | 6.36 | 28.54 | 14.10 | (0.328, 0.640) |
| Comp. Example | H1 | D1 | 7.97 | 22.45 | 8.84 | (0.314, 0.652) |

The invention claimed is:

1. A compound represented by the following Formula 1, 4-4, or 6-4 or the following compound 5 or 7:

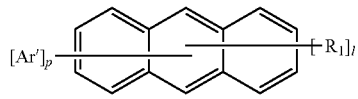

[Formula 1]

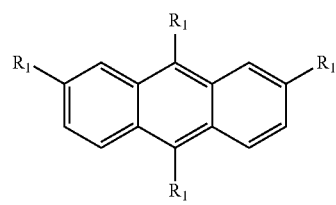

[Formula 4-4]

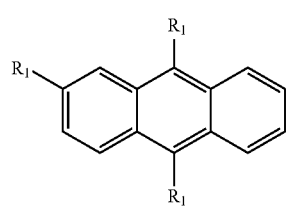

[Formula 6-4]

5

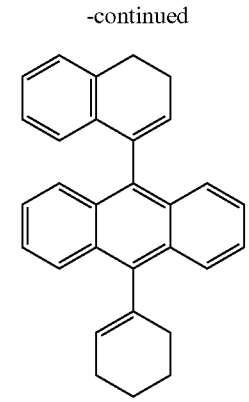

7

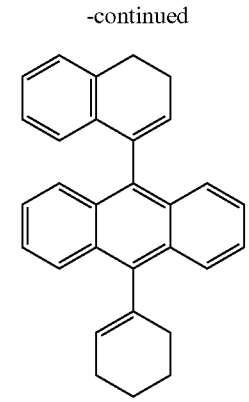

wherein $R_1$ is disposed at a 2, 9 or 10 position of anthracene and a substituent group represented by —[Ar]$_m$—X, p is an integer of 1 to 3, l is an integer of 1 to 4, and m is an integer of 0 to 5, Ar is a $C_6$-$C_{26}$ arylene group that is substituted or unsubstituted by $C_1$-$C_{10}$ alkyl group, a $C_6$-$C_{12}$ aryl group, a $C_2$-$C_{12}$ heterocyclic group including N, O or S as a heteroatom, a silyl group or a $C_1$-$C_{10}$ alkylsilyl group; or a $C_2$-$C_{26}$ divalent heterocyclic group that is substituted or unsubstituted by a $C_1$-$C_{10}$ alkyl group, a $C_6$-$C_{12}$ aryl group, a $C_2$-$C_{12}$ heterocyclic group including N, O or S as a heteroatom, a silyl group or a $C_1$-$C_{10}$ alkylsilyl group, and includes N, O or S as the heteroatom, Ar' is disposed at a 2, 9 or 10 position of anthracene and $C_6$-$C_{26}$ aryl group that is substituted or unsubstituted by a $C_1$-$C_{10}$ alkyl group, a $C_6$-$C_{12}$ aryl group, a $C_2$-$C_{12}$ heterocyclic group that is substituted or unsubstituted by a $C_6$-$C_{12}$ aryl group and includes N, O or S as a heteroatom, a silyl group or a $C_1$-$C_{10}$ alkylsilyl group; or a $C_2$-$C_{26}$ heterocyclic group that is substituted or unsubstituted by a $C_1$-$C_{10}$ alkyl group, a $C_6$-$C_{12}$ aryl group, a $C_2$-$C_{12}$ heterocyclic group that is substituted or unsubstituted by a $C_6$-$C_{12}$ aryl group and includes N, O or S as a heteroatom, a silyl group or a $C_1$-$C_{10}$ alkylsilyl group and includes N, O or S as a heteroatom, X is a substituent group selected from the following Structural Formulas,

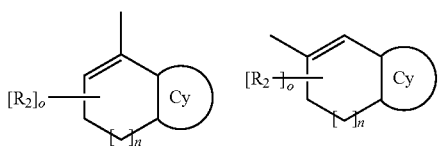

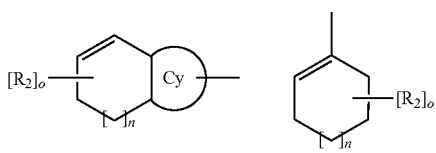

in the Structural Formulas, Cy is a $C_6$-$C_{26}$ aryl group or a $C_2$-$C_{26}$ heterocyclic group including N, O or S as a heteroelement, $R_2$ is selected from the group consisting of a $C_1$-$C_{10}$ alkyl group; and a $C_6$-$C_{26}$ aryl group;

n is an integer of 0 to 5, o is an integer of 0 to 10, and in the case where o is 2 or more, $R_2$s may be the same as or different from each other, and in the case where l, m or p is 2 or more, Ar, Ar', or $R_1$ may be the same as or different from each other.

2. The compound according to claim 1, wherein the compound that is represented by Formula 1 is selected from the group consisting of the following compounds 4-1 to 4-4, 6-1 to 6-4:

[Formula 4-1]
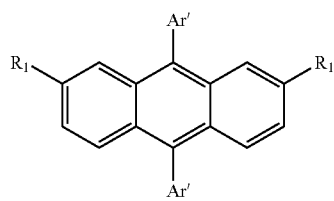

[Formula 4-2]
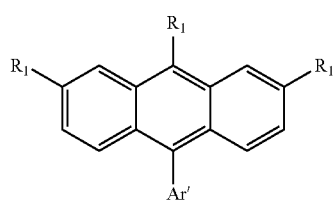

[Formula 4-3]
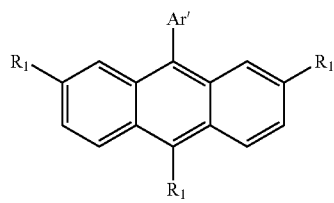

[Formula 6-1]
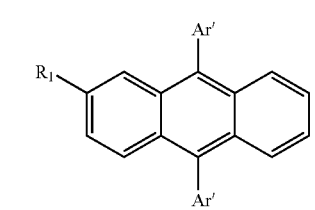

[Formula 6-2]
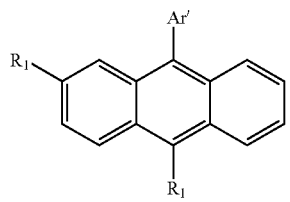

[Formula 6-3]
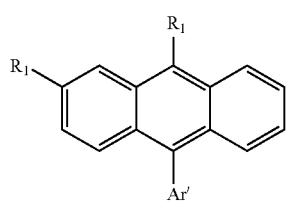

wherein $R_1$s are the same as the definitions of Formula 1, and may be the same as or different from each other, Ar's are the same as the definitions of Formula 1, and may be the same as or different from each other.

3. The compound according to claim 1, wherein the arylene group is selected from the group consisting of a phenylene group, a naphthylene group, a biphenylene group, an anthracenylene group and the following Structural Formulas:

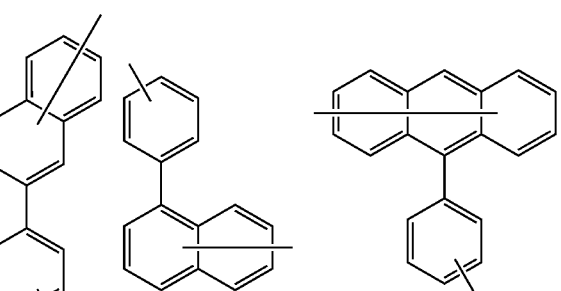

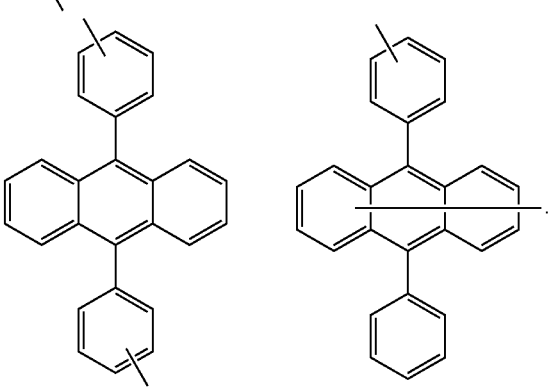

4. The compound according to claim 1, wherein m is 0 or 1.

5. The compound according to claim 1, wherein $R_1$ is selected from the group consisting of the substituent groups represented by the following Structural Formulas:

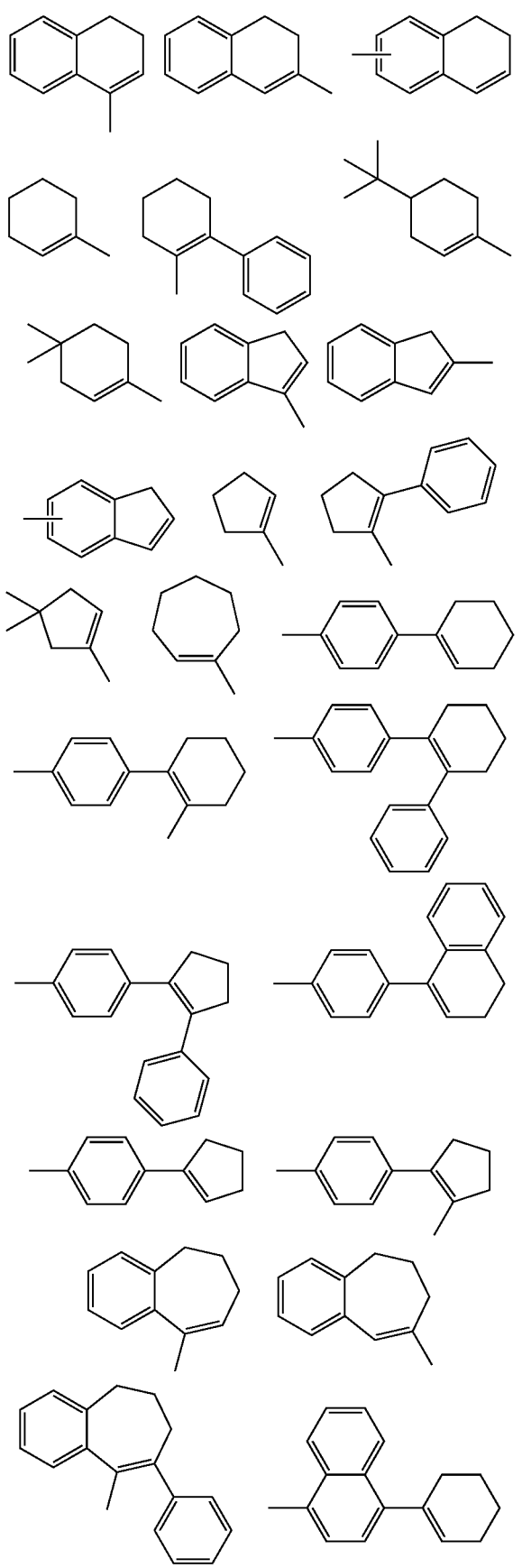
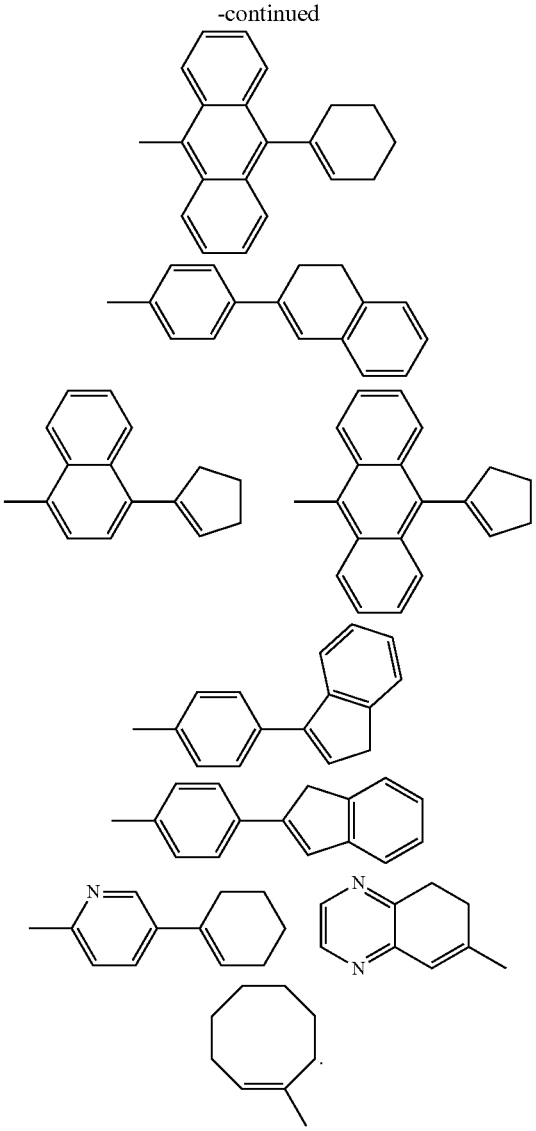
6. The compound according to claim 1, wherein Ar' is selected from the group consisting of the substituent groups represented by the following Structural Formulas:
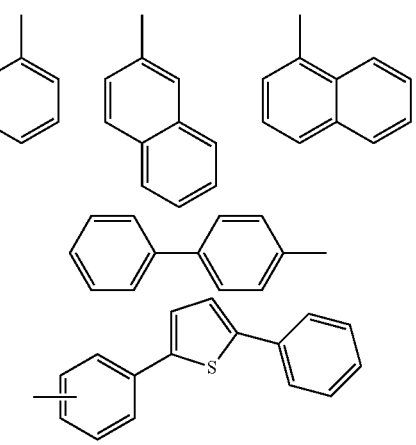

-continued
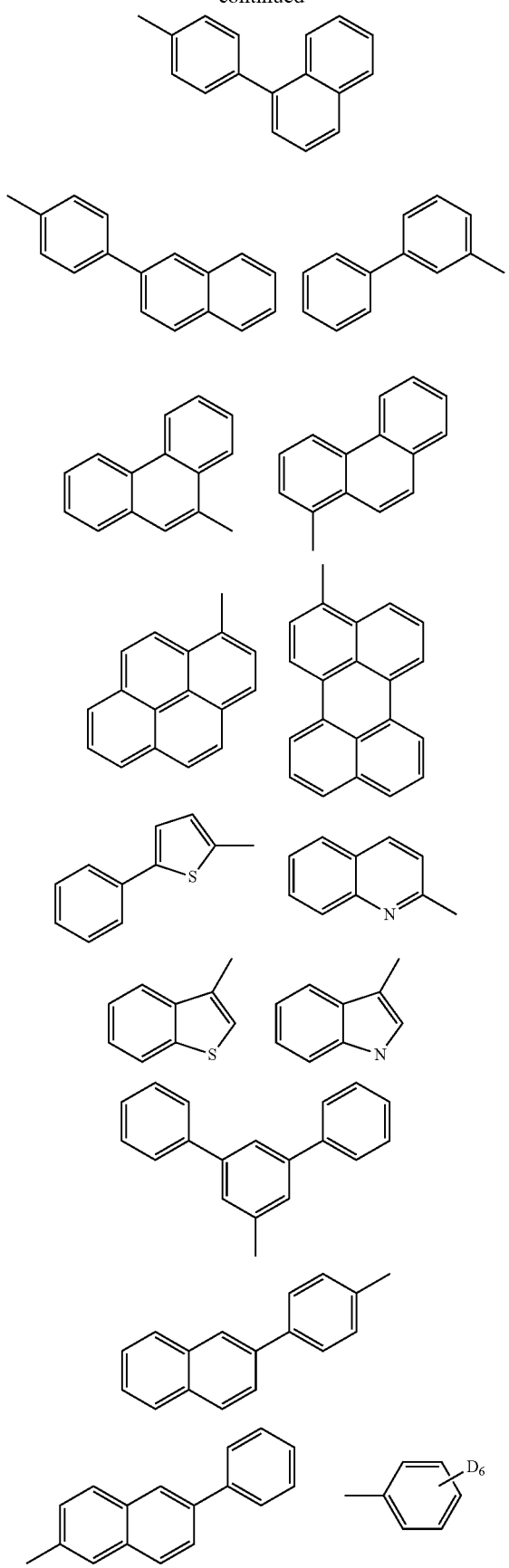
-continued
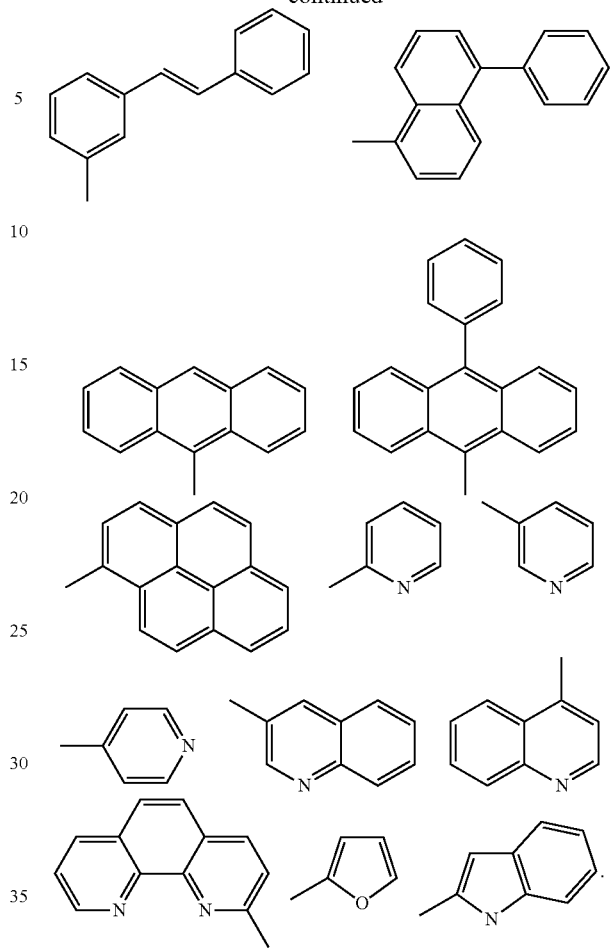
7. The compound according to claim 1, wherein X is selected from the following Formulas, Cy is $C_6$ aryl, and n is 1 or more:
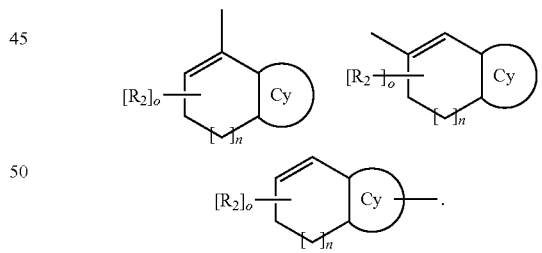
8. The compound according to claim 1, wherein X is represented by the following Formula, $R_1$ is disposed at a 9 position of anthracene of Formula 1, and at least one Ar' is disposed at a 10 position of anthracene:
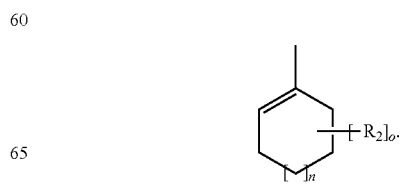

9. The compound according to claim 1, wherein X is represented by the following Formula, p is an integer of 1 to 3, and Ar' is a substituted or unsubstituted $C_6$-$C_{50}$ aryl group or a substituted or unsubstituted $C_2$-$C_{50}$ heterocyclic group including N as a heteroelement:

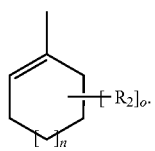

10. The compound according to claim 1, wherein the compound represented by Formula 1 is selected from the group consisting of the following compounds 1 to 4, 8, 11, 13 to 36, 39 to 41, 43 to 69, 72 to 82, 84 to 86:

1

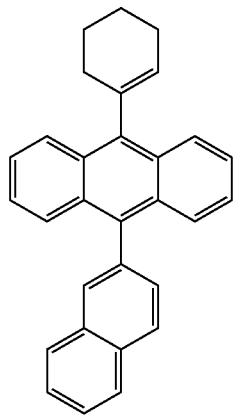

2

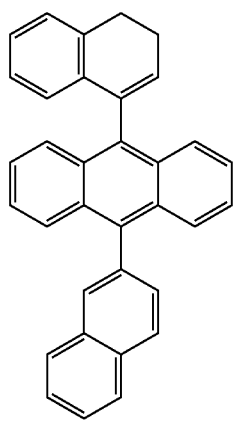

-continued

3

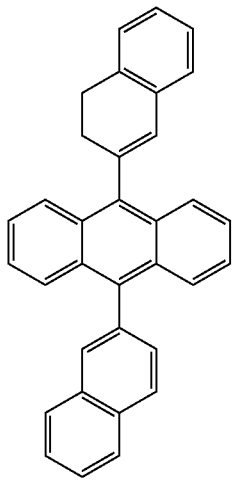

4

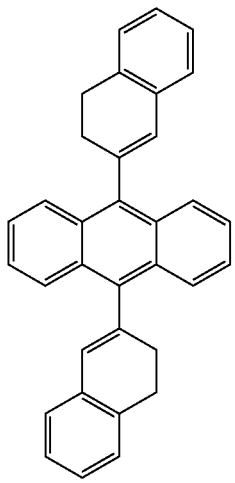

8

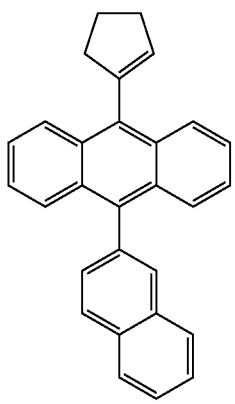

11
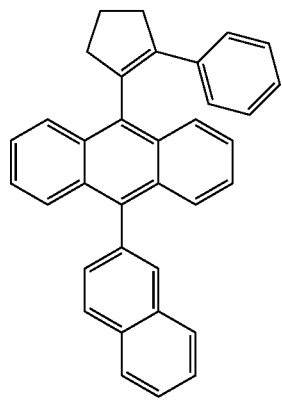
13
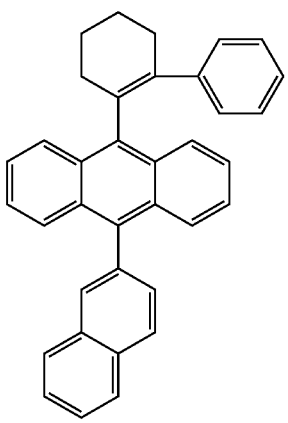
14
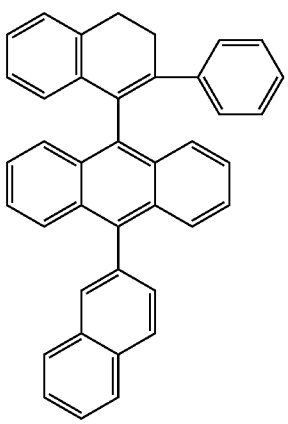
15
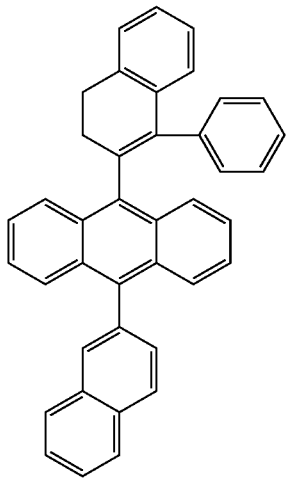
16
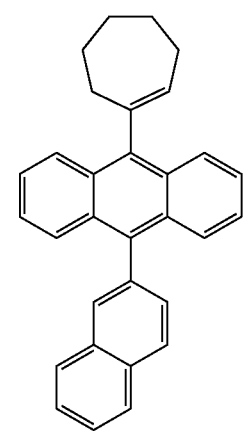
17
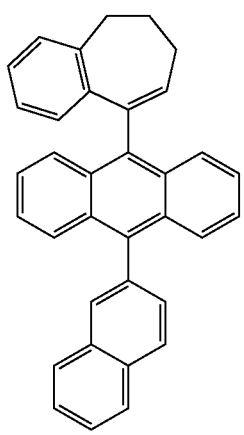

18
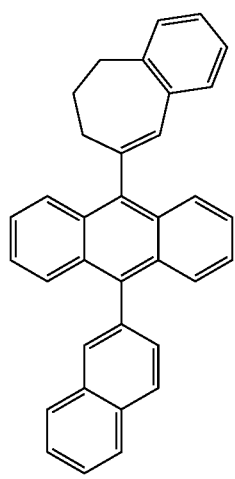
19
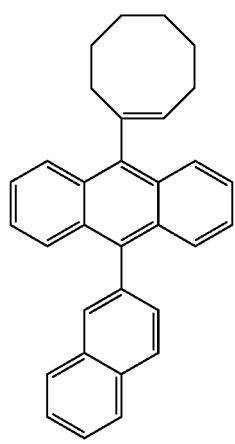
20
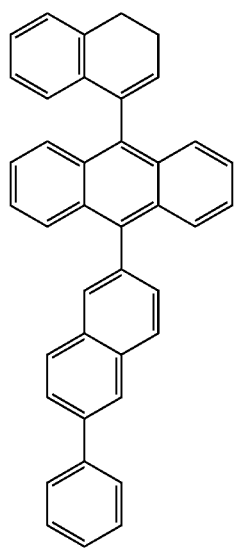
21
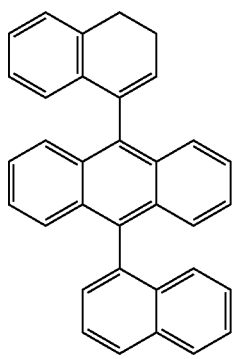
22
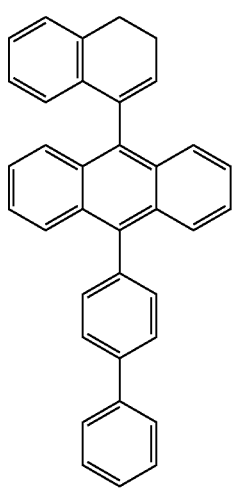
23
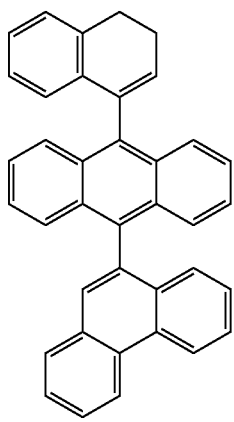

24
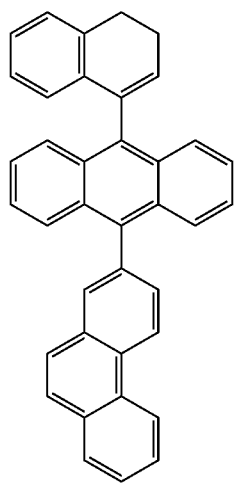
25
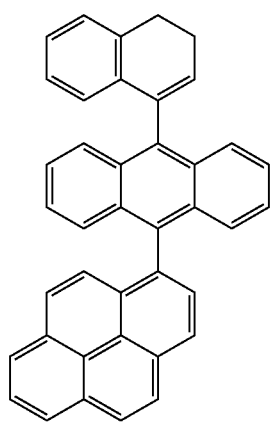
26
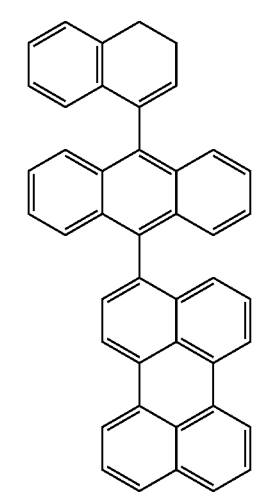
27
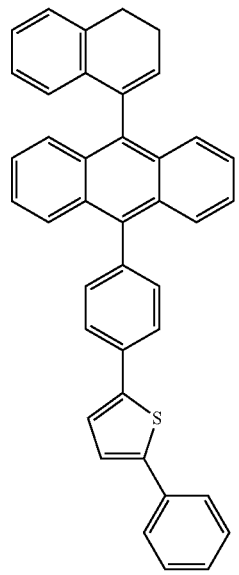
28
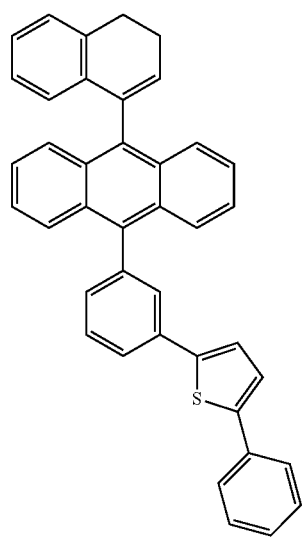
29
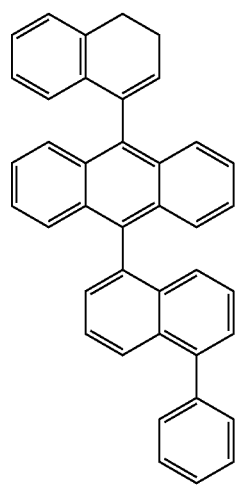

30
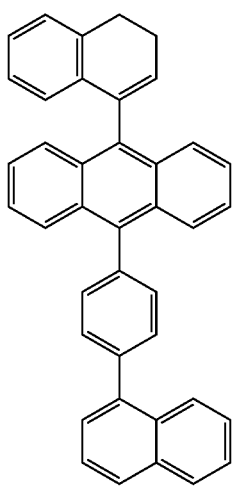
31
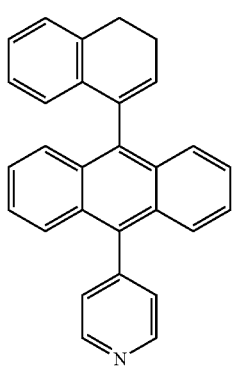
32
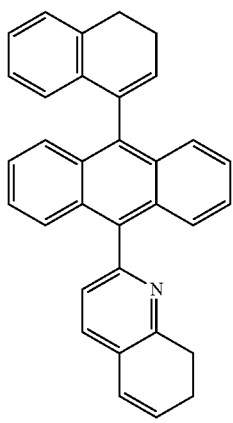
33
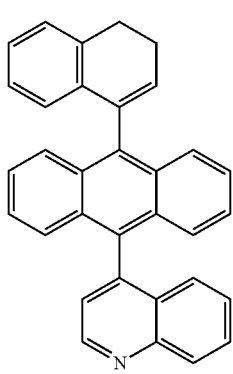
34
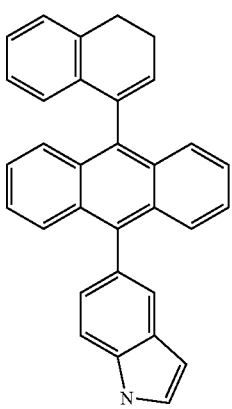
35
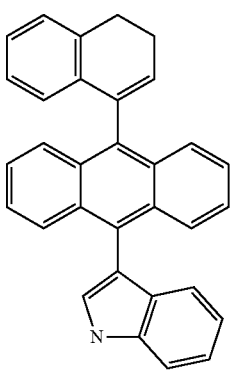
36
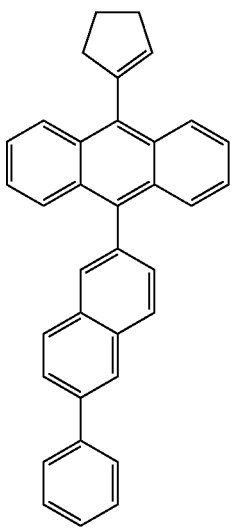

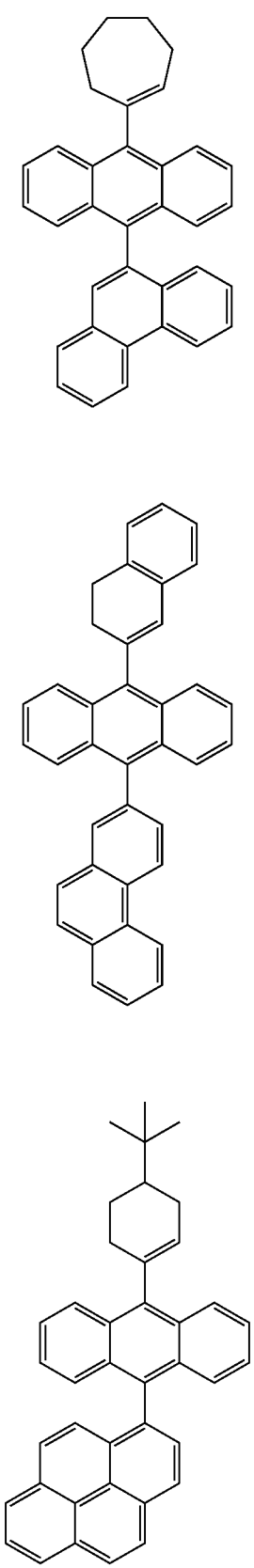
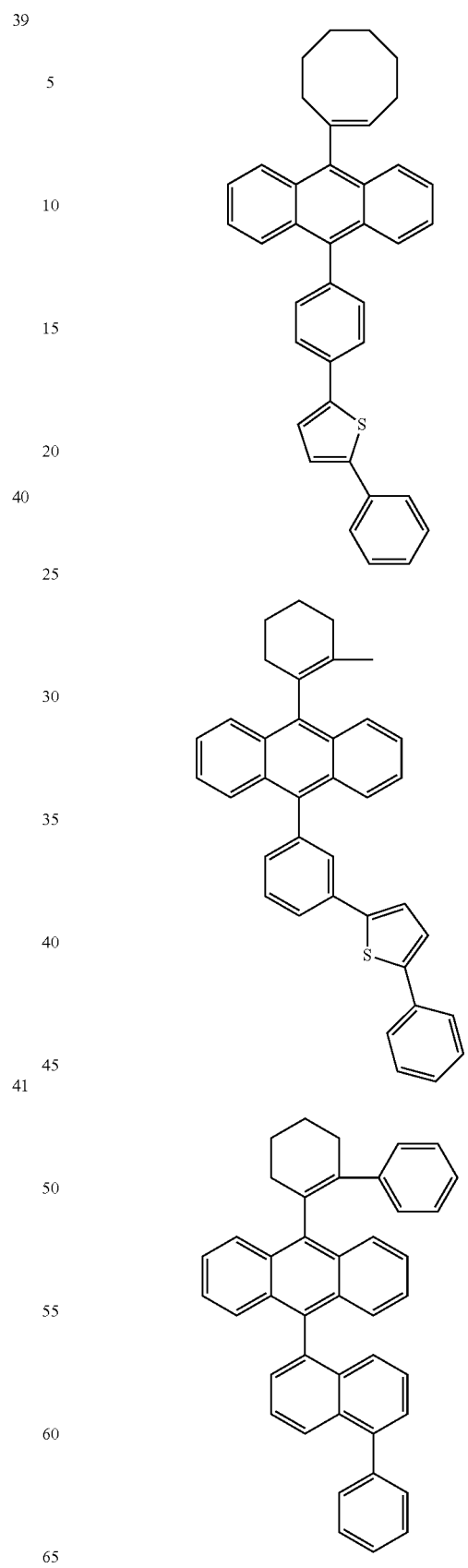

46
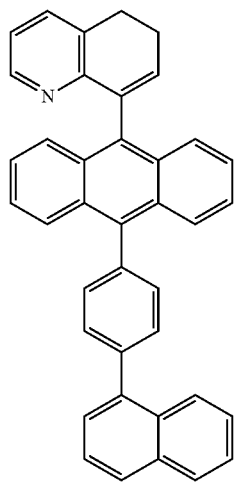
47
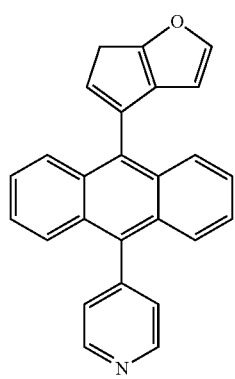
48
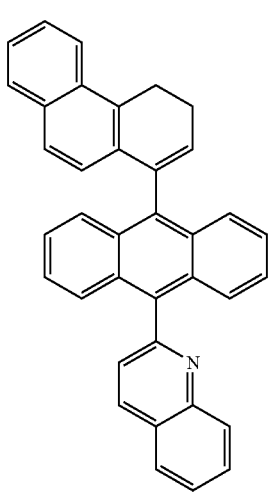
49
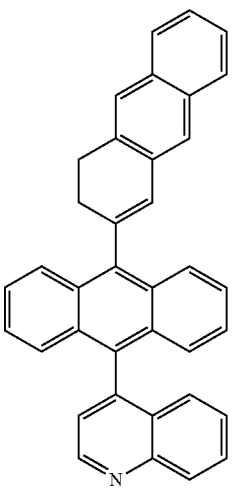
50
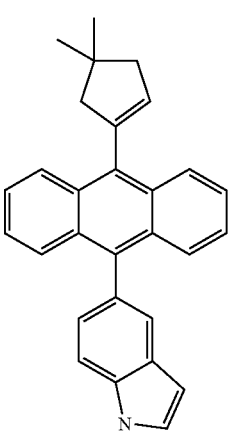
51
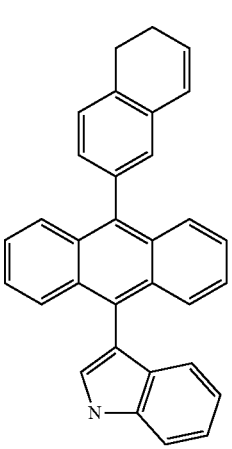

77
-continued
52
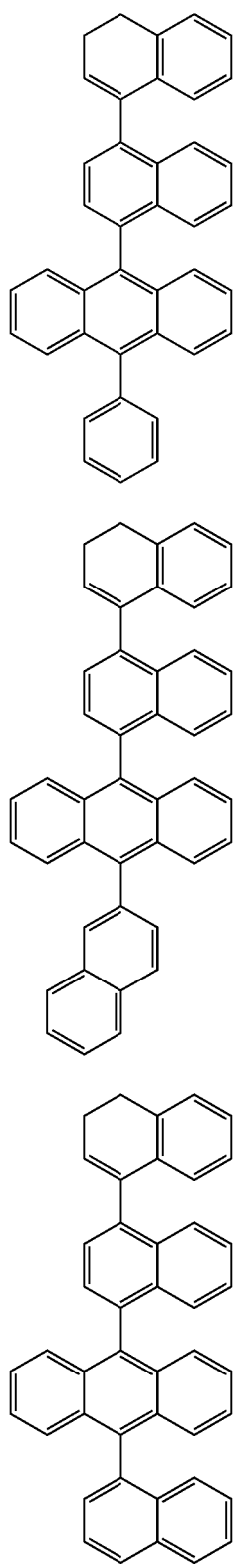
53
54
78
-continued
55
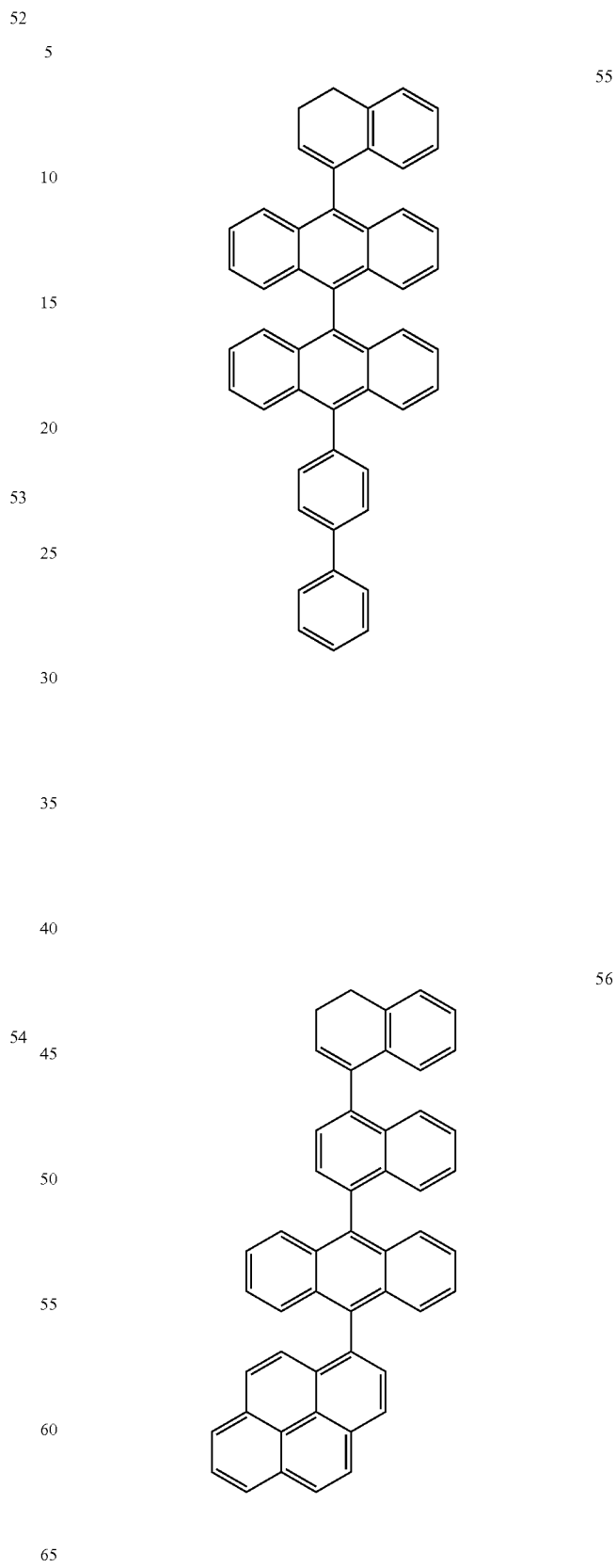
56

57
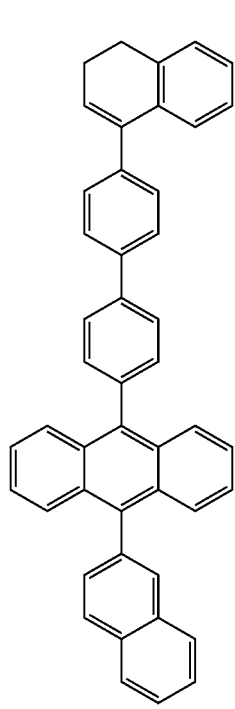
58
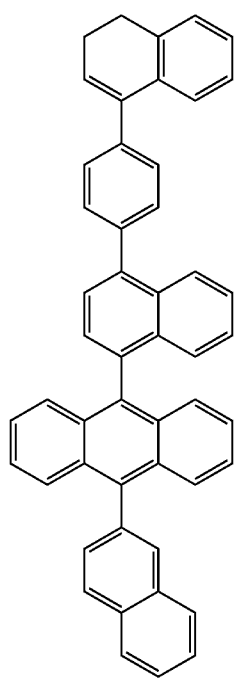
59
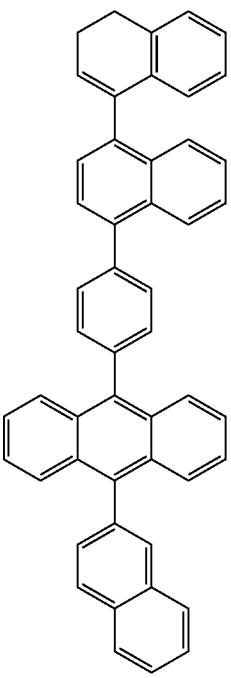
60
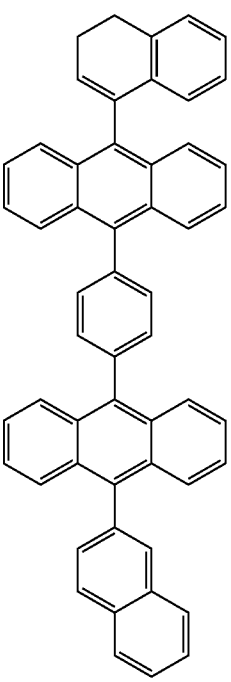

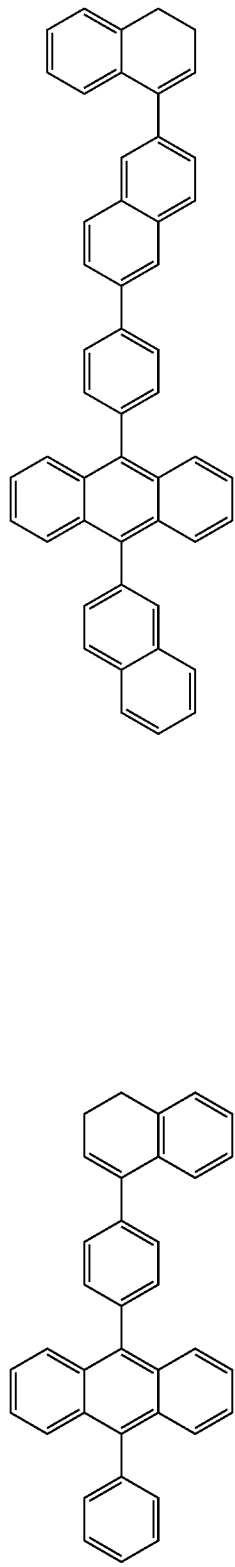
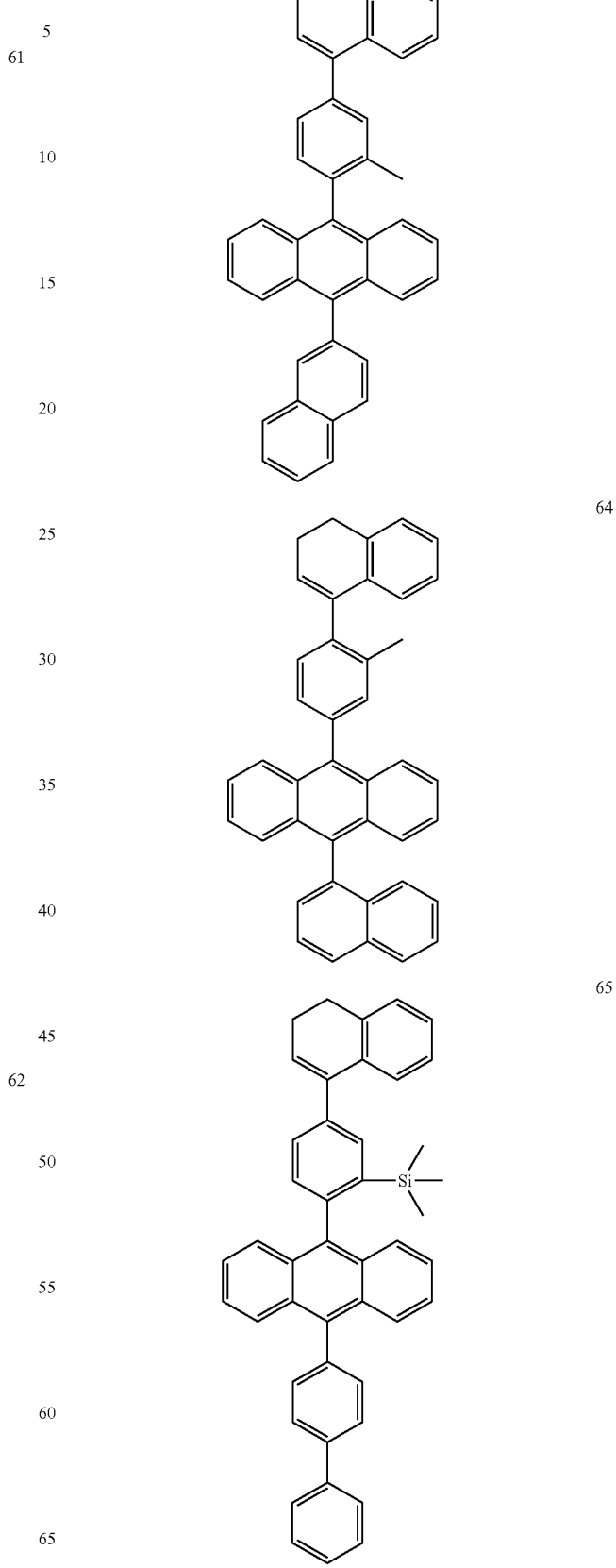

83
-continued
66
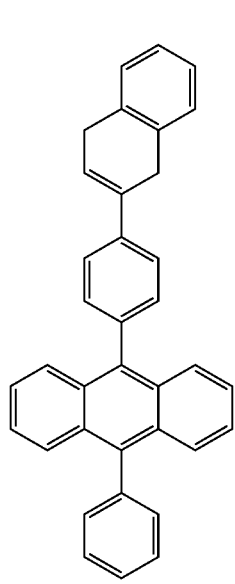
67
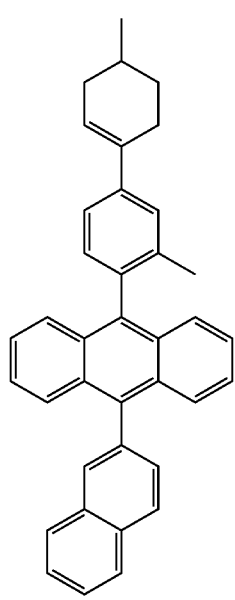
84
-continued
68
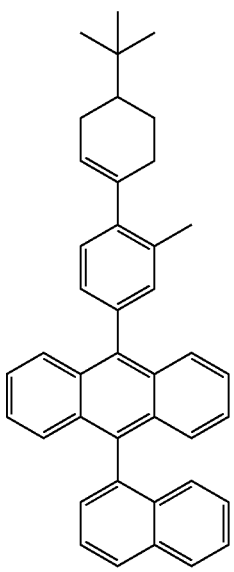
69
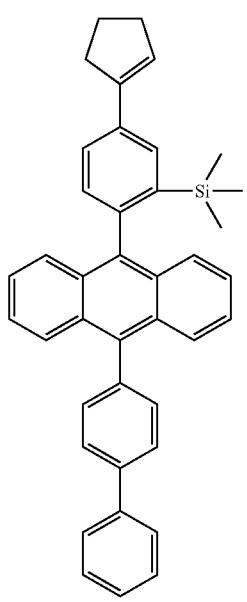

85
-continued
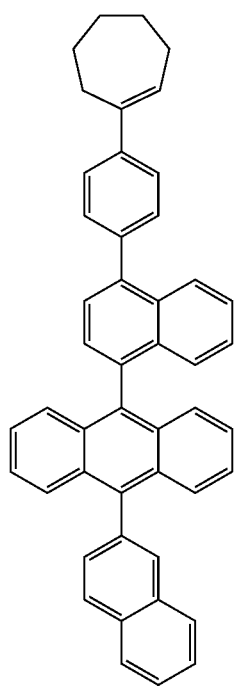
72
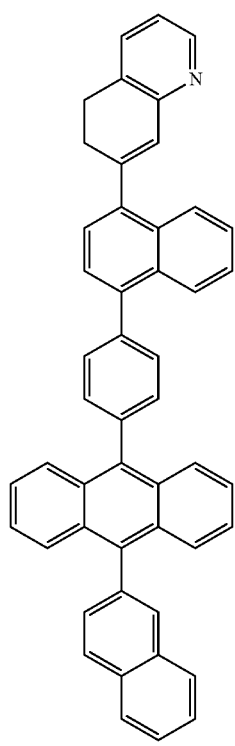
73
86
-continued
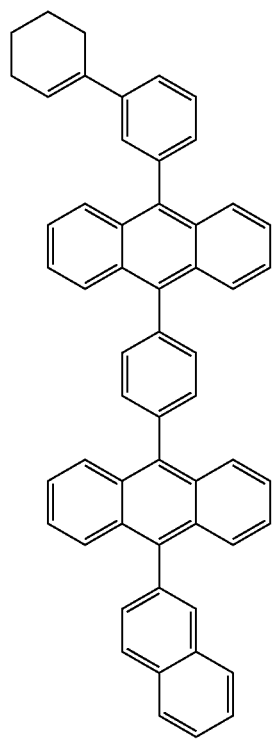
74
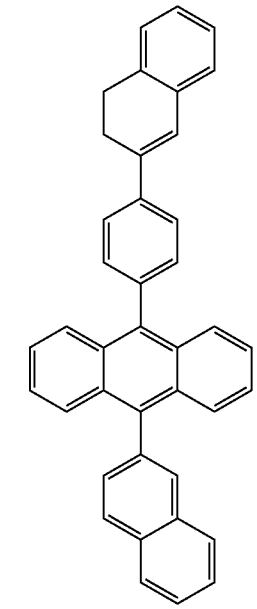
75

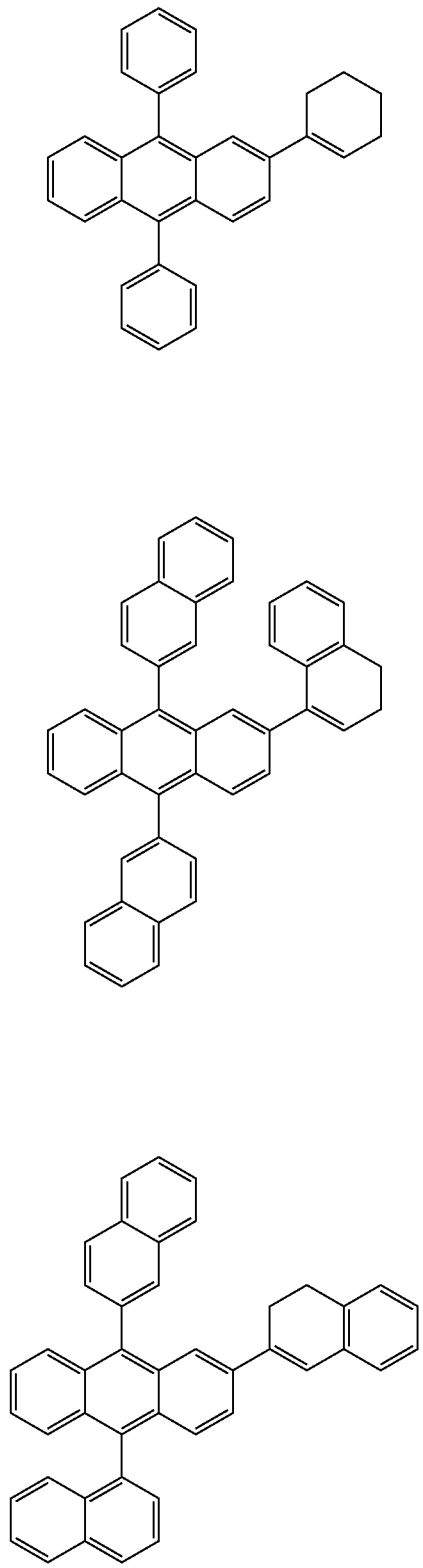
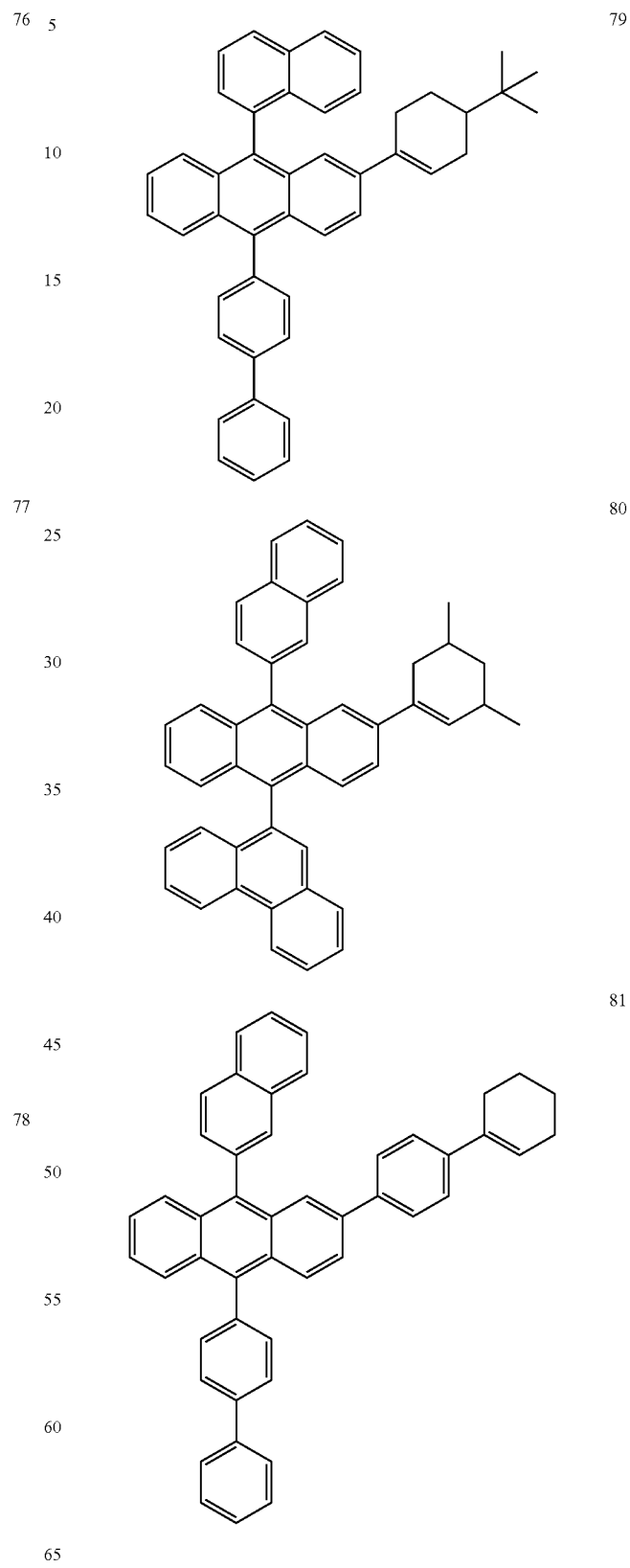

-continued

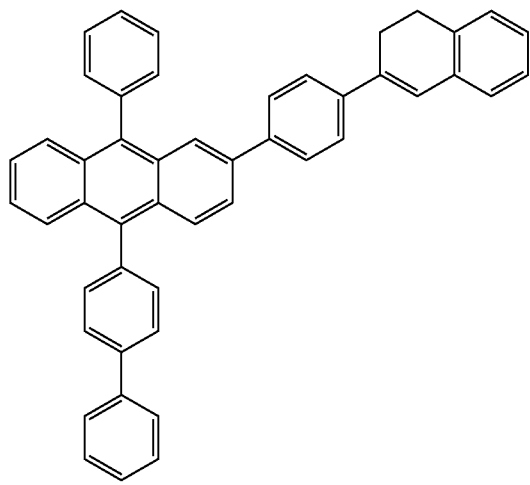
82

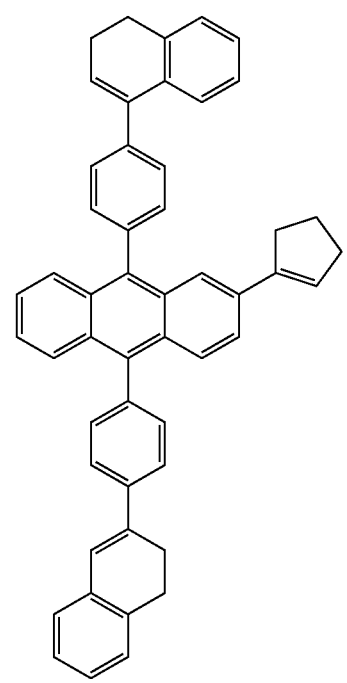
84

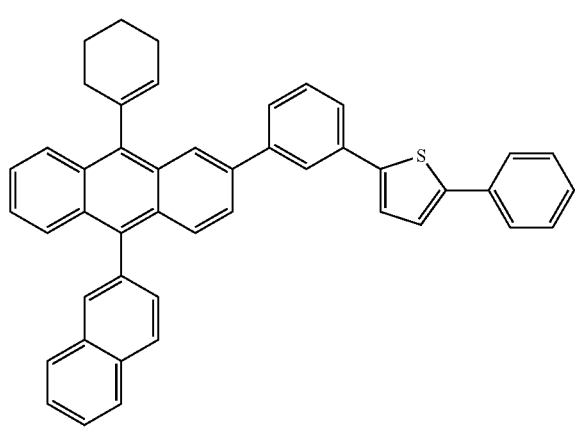
85

-continued

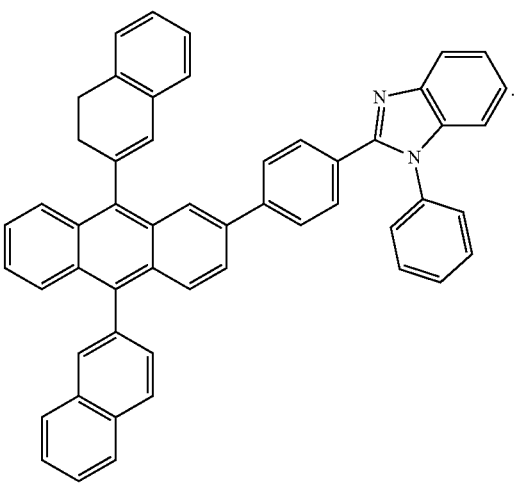
86

11. An organic electronic device which includes a first electrode, a second electrode, and one or more organic material layers that are disposed between the first electrode and the second electrode, wherein one or more layers of the organic material layers include the compound according to claim 1.

12. The organic electronic device according to claim 11, wherein the organic material layer includes an electron injection or transport layer, and the electron injection or transport layer includes the above compound.

13. The organic electronic device according to claim 11, wherein the organic material layer includes a light emitting layer, and the light emitting layer includes the above compound.

14. The organic electronic device according to claim 11, wherein the organic material layer includes a hole injection or transport layer, and the hole injection or transport layer includes the above compound.

15. The organic electronic device according to claim 11, wherein the organic electronic device is selected from the group consisting of an organic light emitting diode, an organic phosphorescent device, an organic solar cell, an organic photoconductor (OPC), and an organic transistor.

16. An organic electronic diode which includes a first electrode, a second electrode, and one or more organic material layers that are disposed between the first electrode and the second electrode, wherein one or more layers of the organic material layers include the compound according to claim 10.

* * * * *